(12) United States Patent
Satterfield et al.

(10) Patent No.: US 10,278,617 B1
(45) Date of Patent: May 7, 2019

(54) METHOD AND APPARATUS FOR SENSING AMMONIA IN BREATH

(71) Applicant: Invoy Holdings, LLC, Chandler, AZ (US)

(72) Inventors: Brent Satterfield, West Bountiful, UT (US); Lubna Ahmad, Chandler, AZ (US); Rhett Martineau, Gilbert, AZ (US)

(73) Assignee: Invoy Holdings, LLC, Aliso Viejo, CA (US)

( * ) Notice: Subject to any disclaimer, the term of this patent is extended or adjusted under 35 U.S.C. 154(b) by 998 days.

(21) Appl. No.: 14/206,146

(22) Filed: Mar. 12, 2014

Related U.S. Application Data

(60) Provisional application No. 61/792,979, filed on Mar. 15, 2013.

(51) Int. Cl.
*A61B 5/08* (2006.01)

(52) U.S. Cl.
CPC .................................... *A61B 5/082* (2013.01)

(58) Field of Classification Search
CPC ...................................................... A61B 5/082
See application file for complete search history.

(56) References Cited

U.S. PATENT DOCUMENTS

| | | |
|---|---|---|
| 3,131,030 A | 4/1964 | Grosskopf |
| 3,350,175 A | 10/1967 | McConnaughey et al. |
| 3,862,420 A * | 1/1975 | Banks ................ G03G 15/0291 250/324 |
| 4,147,514 A | 4/1979 | Magers et al. |
| 4,201,548 A | 5/1980 | Katsuki et al. |
| 4,844,867 A | 7/1989 | Bather |
| 4,931,404 A | 6/1990 | Kundu |

(Continued)

FOREIGN PATENT DOCUMENTS

| | | |
|---|---|---|
| EP | 1 524 522 | 4/2005 |
| WO | WO 03/039367 | 5/2003 |

(Continued)

OTHER PUBLICATIONS

Ahmad, L. et al., "Design of a Breath Ketone Sensor for Obesity Management", Poster Presentation, Fall Meeting of the Biomedical Engineering Society, 2003, in 3 pages.

(Continued)

*Primary Examiner* — Tiffany Weston
*Assistant Examiner* — Tho Q Tran
(74) *Attorney, Agent, or Firm* — Knobbe, Martens, Olson & Bear, LLP

(57) ABSTRACT

A method is provided for sensing ammonia in a breath sample. The method comprises conditioning the breath sample so that the conditioned breath sample has a relative humidity greater than a relative humidity corresponding to a first inflection point of a downwardly concave lowest ammonia iso-concentration curve. It also comprises contacting the conditioned breath sample with an interactant that interacts with the ammonia in the conditioned breath sample, wherein the interaction causes a change in an optical characteristic in relation to the amount of the ammonia in the breath sample. It further comprises using the change in the optical characteristic to sense the ammonia in the breath sample. Related apparatuses are also provided.

21 Claims, 16 Drawing Sheets

(56) References Cited

U.S. PATENT DOCUMENTS

| | | | |
|---|---|---|---|
| 4,947,861 A | 8/1990 | Hamilton | |
| 4,970,172 A | 11/1990 | Kundu | |
| 5,071,769 A | 12/1991 | Kundu et al. | |
| 5,174,959 A | 12/1992 | Kundu et al. | |
| 5,179,052 A | 1/1993 | Knifton | |
| 5,465,728 A | 11/1995 | Phillips | |
| 5,834,626 A | 11/1998 | De Castro et al. | |
| 5,976,467 A * | 11/1999 | Dallas | B01D 53/0454 422/83 |
| 6,010,459 A | 1/2000 | Silkoff et al. | |
| 6,067,989 A | 5/2000 | Katzman | |
| 6,190,858 B1 | 2/2001 | Persaud | |
| 6,206,837 B1 | 3/2001 | Brugnoli | |
| 6,221,026 B1 | 4/2001 | Phillips | |
| 6,234,006 B1 | 5/2001 | Sunshine et al. | |
| 6,254,547 B1 | 7/2001 | Phillips | |
| 6,454,723 B1 | 9/2002 | Montagnino | |
| 6,540,691 B1 | 4/2003 | Phillips | |
| 6,582,376 B2 | 6/2003 | Baghdassarian | |
| 6,599,253 B1 | 7/2003 | Baum et al. | |
| 6,607,387 B2 | 8/2003 | Mault | |
| 6,629,934 B2 | 10/2003 | Mault et al. | |
| 6,658,915 B2 | 12/2003 | Sunshine et al. | |
| 6,726,637 B2 | 4/2004 | Phillips | |
| 6,841,391 B2 | 1/2005 | Lewis et al. | |
| 6,981,947 B2 | 1/2006 | Melker | |
| 7,052,854 B2 | 5/2006 | Melker et al. | |
| 7,104,963 B2 | 9/2006 | Melker et al. | |
| 7,220,387 B2 | 5/2007 | Flaherty et al. | |
| 7,300,408 B2 | 11/2007 | Hancock et al. | |
| 7,364,551 B2 | 4/2008 | Allen et al. | |
| 7,533,558 B2 | 5/2009 | Flaherty et al. | |
| 7,794,994 B2 | 9/2010 | Cranley et al. | |
| 7,837,936 B1 | 11/2010 | Martin | |
| 7,920,998 B2 | 4/2011 | Brown | |
| 7,976,467 B2 | 7/2011 | Young et al. | |
| 8,021,308 B2 | 9/2011 | Carlson et al. | |
| 8,036,708 B2 | 10/2011 | Oozeki | |
| 8,286,088 B2 | 10/2012 | Shaffer et al. | |
| 8,287,454 B2 | 10/2012 | Wolpert et al. | |
| 8,342,178 B2 | 1/2013 | Hengstenberg et al. | |
| 8,399,837 B2 | 3/2013 | Robbins et al. | |
| 8,514,086 B2 | 8/2013 | Harper et al. | |
| 8,680,974 B2 | 3/2014 | Meiertoberens et al. | |
| 8,816,862 B2 | 8/2014 | Harper et al. | |
| 8,848,189 B2 | 9/2014 | Atkin et al. | |
| 8,871,521 B2 | 10/2014 | Akers | |
| 8,917,184 B2 | 12/2014 | Smith et al. | |
| 9,170,225 B2 | 10/2015 | Dutta et al. | |
| 9,173,595 B2 | 11/2015 | Böhm et al. | |
| 2003/0208133 A1 | 11/2003 | Mault | |
| 2004/0018114 A1 | 1/2004 | Wang et al. | |
| 2005/0072213 A1* | 4/2005 | Besnard | G01N 27/127 73/31.06 |
| 2007/0245810 A1 | 10/2007 | Carter et al. | |
| 2007/0258894 A1 | 11/2007 | Melker et al. | |
| 2008/0008666 A1 | 1/2008 | Phillips | |
| 2008/0053194 A1 | 3/2008 | Ahmad | |
| 2008/0234553 A1 | 9/2008 | Urman et al. | |
| 2009/0054799 A1 | 2/2009 | Vrtis et al. | |
| 2010/0301197 A1 | 12/2010 | Boyle | |
| 2011/0028091 A1 | 2/2011 | Higgins et al. | |
| 2011/0098590 A1* | 4/2011 | Garbutt | A61B 5/0059 600/532 |
| 2012/0071737 A1 | 3/2012 | Landini et al. | |
| 2012/0295595 A1 | 11/2012 | Gibori et al. | |
| 2013/0231711 A1 | 9/2013 | Kaib | |
| 2013/0253358 A1 | 9/2013 | Phillips | |
| 2014/0366610 A1 | 12/2014 | Rodriguez | |
| 2015/0073233 A1 | 3/2015 | Rich et al. | |
| 2015/0168307 A1 | 6/2015 | Kück et al. | |
| 2015/0260656 A1* | 9/2015 | Zilberstein | A61B 5/083 436/165 |
| 2015/0289782 A1 | 10/2015 | Peverall et al. | |
| 2016/0146779 A1 | 5/2016 | Gallagher et al. | |
| 2016/0150995 A1 | 6/2016 | Ratto et al. | |

FOREIGN PATENT DOCUMENTS

| | | |
|---|---|---|
| WO | WO 03/039483 | 5/2003 |
| WO | WO 2005/082234 | 9/2005 |
| WO | WO 2010/094967 | 8/2010 |
| WO | WO 2011/104567 | 9/2011 |
| WO | WO 2015/134390 | 9/2015 |

OTHER PUBLICATIONS

Barnett, D. et al., "Breath acetone and blood sugar measurements in diabetes", Clinical Science, vol. 37 (1969), in 1 page.

"CMS Operator Guide", CMS Operator Training 0108, dated Apr. 19, 2002, in 10 pages. URL: http://www.buydraegertubes.com/ds/cms-ops-guide.pdf.

Crofford, O. et al., "Acetone in Breath and Blood", Transactions of the American Clinical and Climatological Association, vol. 88 (1977), in 12 pages.

Davies, S. et al., "Quantitative analysis of ammonia on the breath of patients in end-stage renal failure", Kidney International, vol. 52 (1997), in 6 pages.

Diskin, A. et al., "Time variation of ammonia, acetone, isoprene and ethanol in breath: a quantitative SIFT-MS study over 30 days", Physiological Measurement, vol. 24 (2003), in 13 pages.

Dräger CMS Production Information (document properties of document indicate that the document was created on Dec. 1, 2008), in 4 pages. URL: http://www.draeger.com/sites/assets/PublishingImages/Poducts/cin_chip_measurement_system/US/cms-ds-pi-9044337-en-us.pdf.

DrägerTubes & Accuro Pump Production Information (document properties of document indicate that the document was created on Nov. 11, 2008), in 4 pages, URL: http://www.draeger.com/sites/assets/PublishingImages/Products/cin_accuro/US/081209-pi-DetectorTubes-22-10-2008-en.pdf.

Dubowski, K. et al., "Response of Breath-Alcohol Analyzers to Acetone: Further Studies", Journal of Analytical Toxicology, vol. 8, Sep./Oct. 1984, in 4 pages.

Gervais, T. et al., "Mass transport and surface reactions in microfluidic systems", Chemical Engineering Science, vol. 61 (2006), in 20 pages.

Ketonix US, "Ketonix 2015 Blue Specifications", 2015, in 2 pages. URL:https://www.ketonix/com/index.php/product-2/ketonix-2015-blue.

Ketonix, "Ketonix data for Michel Lundell", 2015, in 1 page. URL: https://www.ketonix.com.

Khan, A. et al. "Evaluation of a bedside blood ketone sensor: the effects of acidosis, hyperglycaemia and acetoacetate on sensor performance", Diabetic Medicine, vol. 21 (2004), in 5 pages.

Kundu, S. et al., "Breath Acetone Analyzer: Diagnostic Tool to Monitor Dietary Fat Loss", Clinical Chemistry, vol. 39 (1993), in 6 pages.

Kundu, S. K. et al., "Novel Solid-Phase Assay of Ketone Bodies in Urine", Clinical Chemistry, vol. 37 (1991), in 5 pages.

Kupari, M. et al., "Breath Acetone in Congestive Heart Failure", The American Journal of Cardiology, vol. 76, Nov. 15, 1995, in 3 pages.

Landini, B. et al., "Breath Acetone Concentration Measured Using a Palm-Size Enzymatic Sensor System", IEEE Sensors Journal, vol. 9, Dec. 2009, in 6 pages.

Landini, B. et al., "Effect of Exhalation Variables on the Current Response of an Enzymatic Breath Acetone Sensing Device", IEEE Sensors Jounal, vol. 10, Jan. 2010, in 6 pages.

Likhodii, S., et al., "Breath Acetone as a Measure of Systemic Ketosis Assessed in a Rat Model of the Ketogenic Diet", Clinical Chemistry, vol. 48 (2002), in 6 pages.

Loken, S. C., "Breath Acetone and Ketone Metabolism in Obese and Diabetic Mice", Diabetes, vol. 25 (1976), in 1 page.

"Figaro Gas Sensor TGS 822", Figaro Engineering Inc., Mar. 1987, in 10 pages.

(56) References Cited

OTHER PUBLICATIONS

"MiniMed 530G System User Guide", Medtronic MiniMed, Inc., 2012, in 312 pages.

Musa-Veloso, K. et al., "Breath acetone is a reliable indicator of ketosis in adults consuming ketogenic meals", The American Journal of Clinical Nutrition, vol. 76 (2002), in 6 pages.

Narasimhan, W. et al., "Correlation of Breath Ammonia with Blood Urea Nitrogen and Creatinine during Hemodialysis", PNAS, vol. 98, Apr. 10, 2001, in 5 pages.

Schwarz, K., et al., "Breath acetone—aspects of normal physiology related to age and gender as determined in a PTR-MS study", Journal of Breath Research, vol. 3 (2009), in 9 pages.

Wang, L. et al., "Nanosensor Device for Breath Acetone Detection", Sensor Letters, vol. 8 (2010), in 4 pages.

Wang, L., "Tailored synthesis and characterization of selective metabolite-detecting nanoprobes for handheld breath analysis", Dissertation Ph. D. Thesis, Stony Brook University, Dec. 2008, in 127 pages.

Yoon, S. et al., "Active control of the depletion boundary layers in microfluidic electrochemical reactors", Lab on a Chip, vol. 6 (2006), in 9 pages.

\* cited by examiner (A) (B)

(C) (D)

METHOD AND APPARATUS FOR SENSING AMMONIA IN BREATH

CROSS REFERENCE TO RELATED APPLICATIONS

This application claims benefit of U.S. Provisional Application No. 61/792,979, filed Mar. 15, 2013, which is hereby incorporated by reference in its entirety.

FIELD OF THE INVENTION

The present invention relates to methods, systems and apparatus for sensing or measuring ammonia in the breath of a patient or "subject" and, preferably, for sensing ammonia in breath using relatively small and inexpensive breathanalysis devices.

BACKGROUND AND RELATED ART

It is well known in the medical arts that certain chemical components ("analytes") in breath are correlated with certain internal physiological and pathophysiological processes or states in the body, and thus such analytes at least in theory can serve as biomarkers for detecting or assessing such processes or states. Risby et al., Current Status of Clinical Breath Analysis, Appl. Phys. (2006), for example, provides a table that lists endogenous breath analytes and the corresponding physiological origin associated with each.

Ammonia in breath has been correlated with several physiological or pathophysiological states. One involves the cellular metabolism of proteins. In the course of metabolism of proteins, the amine groups are converted into ammonia. That ammonia makes its way through the bloodstream to the lungs, where it diffuses across the alveolar membrane into the alveolar air space. As normal respiration occurs, the ammonia-containing air in the lungs is exhaled, where it can be collected and analyzed.

Breath ammonia also is correlated with certain liver pathologies. In the urea cycle, for example, the liver converts ammonia to urea and uric acid. When anomalies in the urea cycle occur, the unreacted ammonia can accumulate and lead to maladies including hepatic encephalopathy. As the ammonia accumulates in the blood, a portion of it passes into the alveolar spaces, from where it is mixed with tidal air and makes its way into exhaled breath.

Another physiological or pathophysiological state that has been correlated with ammonia involves renal dialysis. As reported, for example, in L. R. Narasimhan, William Goodman, and C. Kumar N. Patel, *Correlation Of Breath Ammonia With Blood Urea Nitrogen And Creatinine During Hemodialysis*, PNAS, Vol. 98, No. 8, pgs. 4617-4621, Apr. 10, 2001, breath ammonia concentration has been correlated with blood-urea-nitrogen ("BUN") levels. BUN levels are used clinically during dialysis treatments to assess the adequacy of the dialysis process. Narasimhan et al. report that breath ammonia levels drop by around 90% during the first 30 minutes of hemodialysis and correlate well with BUN and creatinine levels. The use of breath ammonia to make this assessment allows a real time or near-real time measure, as opposed to the non-real time and only periodic testing associated with BUN measurement using blood samples.

Breath ammonia also can be used to detect and assess end-stage renal failure. As renal function decays during such failure, nephrons fail to remove nitrogen-bearing wastes from the blood. The resultant elevated levels of nitrogenous wastes, including ammonia, travel through the bloodstream and eventually pass through the lung barrier into the alveolar air, and into exhaled breath. While a healthy population may have breath ammonia levels of less than about 100 parts per billion ("ppb"), patients with end stage renal failure can reach breath ammonia levels of 13,000 ppb. David Smith, Tianshu Wangl, Andriy Pysanenkol, Patrik Španěll, *A Selected Ion Flow Tube Mass Spectrometry Study of Ammonia in Mouth-and Nose-Exhaled Breath and In the Oral Cavity*; S. Davies, P. Španěl and D. Smith, *Quantitative Analysis Of Ammonia On The Breath Of Patients In End-Stage Renal Failure*," Kidney Int. 52, 223-228 (1997).

Breath ammonia also has been correlated with certain forms of gastritis and gastrointestinal ulcers. U.S. Pat. No. 4,947,861, issued to Hamilton on Aug. 14, 1990 ("Hamilton") at col. 1, for example, reports that "[i]t is a relatively recent discovery that a colony of *Campylobacter pylori* [(or *C. pylori*, now *Helicobacter pylori* or *H. pylori*)] bacteria is usually found associated with gastritis and duodenitis, and is frequently found at the sites of peptic and duodenal ulcers." According to Hamilton, "Graham et al. reported successful results with a breath test wherein patients first ingested urea labeled with carbon-13, a stable, naturally occurring non-radioactive isotope. In the presence of urea, *C. pylori* produces urease, an enzyme that breaks down urea into ammonia, carbon dioxide and other products." Some portion of the ammonia generated at the gastrointestinal site is then transported via the vascular system to the lungs, where it enters the alveolar air space and is exhaled in the breath. (See, also, U.S. Pat. No. 5,179,052 to Ito et al.)

The sensing of breath ammonia, however, presents several challenges. One such challenge is attributable in part to the low levels or concentrations of the ammonia typically in breath, even under pathophysiological states. Another involves the fact that breath ammonia is accompanied by water or humidity, wherein the water is in great excess. Ammonia is highly soluble in water. Given the extremely close molecular weight of the two (17 for ammonia versus 18 for water), they present challenges in separation, detection, masking, etc. This molecular weight similarity makes their fractionation products virtually indiscernible with a mass spectrometer.

A number of technical approaches have been used to sense ammonia in breath. One such technique involves the use of gas chromatography ("GC"). This technique is limited, however, particularly where field or home use is required or desirable, in that GC equipment is relatively large, expensive, and requires trained technicians to operate. These factors confine GC largely to laboratory or hospital settings. Notwithstanding this, generally-accepted GC methods have been relatively unsuccessful for sensing ammonia in breath because of the presence of relatively high concentrations of water and the low concentrations of ammonia.

Newer methods, such as selected ion flow tube-mass spectrometry ("SIFT-MS"), are capable of detecting ammonia at the low levels present in breath in essentially real time. Such instruments, however, are expensive, typically costing in excess of $200,000, they are relatively inaccessible given how few are in existence, they weigh over 200 kilograms ("kg"), and they currently do not have regulatory approval for breath analysis. Again, they are highly unsuited for field or home use.

Another approach for sensing of breath ammonia has involved the use of pH indicators. Such indicators have been used for many decades in the detection of various acidic and basic gases in the ambient air. U.S. Pat. No. 3,131,030 to Grosskopf, for example, discloses impregnating polystyrene beads with methyl violet for detection of the basic gas hydrazine. U.S. Pat. No. 3,350,175 to McConnaughey discloses impregnating clay spheres with thymol blue and oxalic acid, which are then adsorbed to 60 to 80 mesh glass spheres for the detection of ammonia. McConnaughey reports a detection limit of just under 250 parts per million ("ppm"), which is substantially less sensitive than the levels typically required for sensing ammonia in breath. U.S. Pat. No. 4,201,548 to Katsuki discloses impregnating a polyethylene tape with bromocresol green. Katsuki reports the ability to detect ammonia at levels near 500 ppb in liquid samples, but not in breath. U.S. Pat. No. 4,947,861 (Hamilton) discloses using a Gastec® ammonia tube (cresol red pH indicator with a 1,000 ppb preferred detection limit) connected to an Ascarite II® (registered trademark of Authur H. Thomas Co.) desiccant to detect ammonia produced by *H. pylori* bacteria in the digestive tract.

In view of the foregoing, there is a clear need for improved devices and methods that can enable one to sense breath ammonia down to the concentration ranges in which ammonia is present in breath during various physiological and pathophysiological states, e.g., at levels of 0.2 ppm and below. Such devices and methods preferably would be able to sense ammonia in breath samples that comprise water, carbon dioxide and other chemical constituents, and still have the sensitivity and discrimination capabilities to accurately and reliably measure the ammonia.

There also is considerable advantage in providing such breath analysis devices and methods that can accurately and reliably sense ammonia in a clinical, field or patient home setting, which implicates a need for small or portable, cost-effective devices and components, and methods that lend themselves to such applications.

SUMMARY OF THE INVENTION

To address these limitations and to advance the art, a method is provided for sensing ammonia in a breath sample. The method comprises conditioning the breath sample so that the conditioned breath sample has a relative humidity greater than a relative humidity corresponding to a first inflection point of a downwardly concave lowest ammonia iso-concentration curve. It also comprises contacting the conditioned breath sample with an interactant that interacts with the ammonia in the conditioned breath sample, wherein the interaction causes a change in an optical characteristic in relation to the amount of the ammonia in the breath sample. It further comprises using the change in the optical characteristic to sense the ammonia in the breath sample.

The conditioned breath sample preferably has a relative humidity greater than a relative humidity corresponding to the first inflection point plus a margin. Also, the conditioned breath sample may have a relative humidity (a) greater than a first midpoint that is half of the distance along the lowest ammonia iso-concentration curve between the first inflection point and a peak of the lowest ammonia iso-concentration curve, (b) substantially equal to the relative humidity corresponding to the peak of the lowest ammonia iso-concentration curve, (c) greater than a peak of the lowest ammonia iso-concentration curve, (d) greater than a relative humidity corresponding to a second midpoint that is half of the distance along the lowest ammonia iso-concentration curve between a peak and a second inflection point of the lowest ammonia iso-concentration curve, (e) within a range of between a relative humidity corresponding to the first inflection point of the lowest ammonia iso-concentration cure and a relative humidity of a second inflection point of the lowest ammonia iso-concentration curve, (f) within a range of between a relative humidity corresponding to the first inflection point of the lowest ammonia iso-concentration cure and a relative humidity of a peak of the lowest ammonia iso-concentration curve, (g) within a range of between a relative humidity corresponding to a peak of the lowest ammonia iso-concentration cure and a relative humidity of a second inflection point of the lowest ammonia iso-concentration curve, and (h) within a range of between a relative humidity corresponding to a first midpoint that is half of the distance along the lowest ammonia iso-concentration curve between a first inflection point and a second inflection point of the lowest ammonia iso-concentration.

In other implementations, the conditioned breath sample has a relative humidity corresponding to a maximum change in the optical characteristic.

Different implementations involve contacting the breath sample with a granular desiccant. The granular desiccant preferably has a mesh size of at least 4 or between 4 and 30.

The interactant of the illustrative implementation may comprise an ammonia-reactive indicator that changes color as ammonia interacts with the ammonia-responsive indicator. The ammonia-reactive indicator may comprise a pH indicator. The pH indicator is sometimes coupled to a silica gel substrate where the silica gel substrate can have a mesh size of between 20 and 200.

The interactant may be a pH indicator with a pKa of less than 8. It may also be bromophenol blue.

The optical characteristic described above comprises an intensity at a predetermined optical frequency, although sometimes a range of frequencies may be used.

An apparatus is also provided for sensing ammonia in a breath sample. The apparatus comprises a breath conditioning device, an interactant region, and a sensor. The breath conditioning device receives the breath sample and conditions the breath sample so that the conditioned breath sample has a relative humidity greater than a relative humidity corresponding to a first inflection point of a downwardly concave lowers ammonia iso-concentration curve. The interactant region receives the conditioned breath sample and causes the conditioned breath sample to interact with an interactant that interacts with the ammonia in the conditioned sample wherein the interaction causes a change in an optical characteristic of the interactant region in relation to the amount of the ammonia in the breath sample. The sensor senses the change in the optical characteristic and generates an output representative of the change in the optical characteristic.

The breath conditioning device conditions the breath sample so that the conditioned breath sample has a relative humidity in the ranges described above. An example is that the relative humidity is greater than a relative humidity corresponding to the first inflection point plus a margin. Another example is greater than a first midpoint that is half of the distance along the lowest ammonia iso-concentration curve between the first inflection point and a peak of the lowest ammonia iso-concentration curve.

The apparatus preferably includes a granular desiccant, typically between mesh sizes of 4 and 30.

The interactant may comprise an ammonia-reactive indicator that changes color as ammonia interacts with the ammonia-responsive indicator. It may also comprise a pH indicator, such as one coupled to a silica gel substrate, and further that may have a pKa of less than 8. The silica gel substrate preferably has a mesh size of between 20 and 200. The interactant may comprise bromophenol blue.

The optical characteristic comprises an intensity at a predetermined optical frequency.

The breath conditioning device may condition the breath sample so that the amount of the water vapor in the prepared breath sample corresponds to a relative humidity of greater than 1% and less than 100% or, alternatively, between 50% and 90%.

Optionally, the apparatus may comprise a processor operatively coupled to the sensor that uses the signal to assess at least one of the presence and the amount of the ammonia in the breath sample.

According to another aspect of the invention, a method is provided for making a breath sensing device for sensing ammonia in a breath sample. The method comprises coupling an ammonia-reactive indicator to a substrate, wherein the ammonia-reactive indicator has a pKa of less than 8. It further comprises contacting the ammonia-reactive indicator and the substrate with an acid having at least two available protons to form an interactant, wherein the pKa for the dissociation of a first one of the protons is less than the pKa of the ammonia-reactive indicator, wherein the boiling point of the acid in a 99% pure form is greater than 37° C. at standard atmospheric pressure, and wherein the interactant is configured to interact with the ammonia in the breath sample to yield a product, and to cause a change in an optical characteristic between the interactant and the product in relation to the amount of the ammonia that interacts with the interactant. It further comprises disposing the ammonia-reactive indicator and the substrate in an interactant region of a sensor that is configured to receive the breath sample.

A breath analysis system that utilizes the methods described herein is provided. The breath analysis system comprises a base with a detachable cartridge comprising an interactant region. The interactant region receives the conditioned breath sample and causes the conditioned breath sample to interact with an interactant that interacts with the ammonia in the conditioned sample. The interaction causes a change in an optical characteristic of the interactant region in relation to the amount of the ammonia in the breath sample. The base comprises a sensor that senses the change in the optical characteristic and generates an output representative of the change in the optical characteristic.

A breath sample containing device can work in conjunction with the breath analysis system. The breath sample containing device comprises a breath sample container, a breath sample input, and a breath conditioning device. The breath sample container comprises a coupler for detachably coupling the breath sample container to the breath analysis device. The breath sample input is coupled to and in fluid communication with the breath sample container. The breath conditioning device receives the breath sample from the input and conditions the breath sample so that the conditioned breath sample has a relative humidity greater than a relative humidity corresponding to a first inflection point of a downwardly concave lowest ammonia iso-concentration curve.

BRIEF DESCRIPTION OF DRAWINGS

The accompanying drawings, which are incorporated in and constitute a part of the specification, illustrate a presently preferred embodiments and methods of the invention and, together with the general description given above and the detailed description of the preferred embodiments and methods given below, serve to explain the principles of the invention. Of the drawings.

DETAILED DESCRIPTION OF THE PREFERRED EMBODIMENTS AND METHODS OF THE INVENTION

Figure 1:
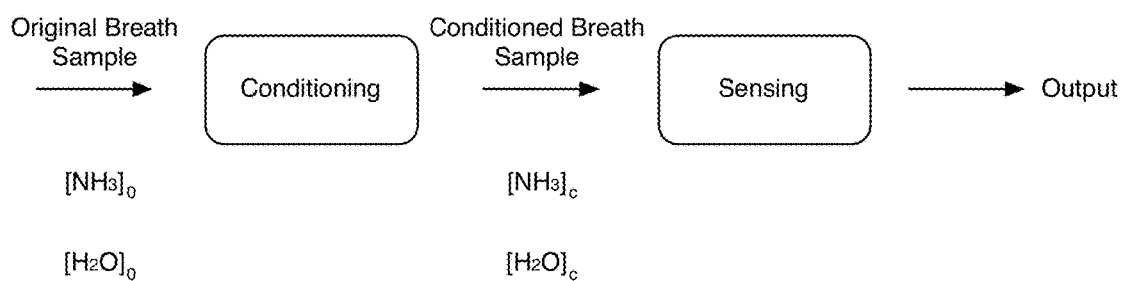
FIG. 1 is a functional block diagram of breath analysis that illustrates aspects of the invention.

Reference will now be made in detail to the presently preferred embodiments and methods of the invention as described herein below and as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the preferred embodiments and methods. The invention according to its various aspects is particularly pointed out and distinctly claimed in the attached claims read in view of this specification, and appropriate equivalents.

In accordance with the invention, apparatus and methods are provided for sensing ammonia as an analyte in a breath sample. "Breath" as used herein is used according to its broad but common meaning in the field and includes any gas generated by or emanating from the respiratory system of the body. "Gas" as the term is used herein also is used broadly and according to its common meaning to include not only pure gas phases but also vapors, non-liquid fluid phases, gaseous colloidal suspensions, solid phase particulate matter or liquid phase droplets entrained or suspended in gases or vapors, and the like. Although as a general matter the term "breath" may comprise gas in the upper airways such as nasal passages, bronchial space, etc., for present purposes it preferably comprises primarily or exclusively gas from the alveolar space, as would be exhaled by a subject under normal circumstances and respiratory conditions. The term "breath sample" is used here in its common but broad meaning to include a sample of the breath of the subject or patient that is to be analyzed. The breath sample may comprise a single exhalation, a plurality of exhalations, a plurality of breaths, one or more portions or segments of any of these, and the like. The term "analyte" is used broadly herein to mean a chemical component or constituent that is sought to be sensed, such as ammonia. An analyte may be or comprise an element, compound or other molecule, an ion or molecular fragment, or other substance that may be contained within a fluid. In some instances, embodiments and methods, there may be more than one analyte present, and an objective is to sense multiple analytes. "Sense" and "sensing" as the terms are used in this document are used in their common but broad interpretations to mean detecting the presence of the analyte or analytes of interest, (here ammonia), to measure the amount or concentration of ammonia, or to otherwise characterize the ammonia. "Sense" and "analyze" are used interchangeably herein.

As has been noted herein above, human breath typically comprises many chemical constituents or analytes. Although the process is dynamic, wherein a person inhales ambient air, gas exchange occurs in the lungs, and the gas from the lungs and associated airways is exhaled as the gas exchange process is completed, the following table provides the major components of both ambient air and alveolar air and their approximate percentages for a typical set of circumstances.

TABLE 1

| GAS | AMBIENT AIR (%) | ALVEOLAR AIR (%) |
| --- | --- | --- |
| Nitrogen ($N_2$) | 78.6 | 74.9 |
| Oxygen ($O_2$) | 20.9 | 13.7 |
| Carbon Dioxide ($CO_2$) | 0.04 | 5.2 |
| Water ($H_2O$) | 0.46 | 6.2 |

As this table shows, exhaled alveolar air as would be found in an original breath sample obtained from a patient includes a relatively substantial amount of water vapor. Some small portion may be in liquid form, e.g., as droplets suspended in the gas phase. Most of it, however, will be in the form of water vapor. This water vapor may be expressed in terms of a relative humidity.

In certain states, the breath also will include measurable amounts of ammonia gas. The presence and concentration of ammonia in the breath of a given individual will depend on a number of factors, including, for example, the patient's physiological state, diet, exercise, the existence, nature and extent of certain pathophysiological states, etc. Under normal circumstances with a healthy patient, concentrations of ammonia in breath averaged over a full exhalation normally are in a range of about 100 ppb or less. As noted herein above, a patient that is in end stage renal failure may have a breath ammonia concentration in a range of as high as 13,000 ppb or higher.

In sensing breath ammonia, particularly given the typically low concentrations of ammonia found in human breath, it is important to avoid loss or "stripping" of the ammonia present in the sample, particularly from the effects of water. Ammonia is highly soluble in water and water, particularly liquid-phase water, plays an important role in this ammonia stripping.

As noted herein above, breath usually comprises a relatively substantial amount of water or moisture. The moisture includes water vapor and also typically includes liquid water or saliva droplets suspended or otherwise contained in the breath gas. In human patients, exhaled breath typically is at or near a temperature of about 37° C. (98.7° F.) with a relative humidity of about 100%. As the breath is exhaled, and particularly when it is collected in a breath collection vessel at or near ambient or room temperature of about 25° C. (77° F.), water condensation occurs and liquid water may adhere to or coalesce on the walls or solid surfaces of the vessel interior. In addition, if the vessel interior or the gas (if any) in the vessel interior is at a temperature lower than the breath temperature, or if the pressure is higher than that of the breath sample, some of the water vapor in the breath sample may condense out to form liquid water.

Given the high solubility of ammonia in water, if liquid water is present in the breath sample containment vessel, ammonia gas present in the breath sample will dissolve into the aqueous phase and thus be removed from the gas-phase breath sample. This problem is compounded where there are large effective surface areas, such as in filters, certain flow restrictors, packed beds, and other highly-porous or channeled media. In view of the approximately 100% relative humidity at 37° C. that is common for exhaled breath samples and the fact that most sensing devices will have at least one segment or component that is well below the 37° C. temperature of exhaled air, some condensation is almost inevitable. Even a small filter with high surface area presents a risk of extracting nearly all of the ammonia from a breath sample if condensation is allowed to form on it. This of course will cause the breath ammonia sensing to misrepresent the amount of ammonia gas in the original breath sample.

The carbon dioxide in human breath can worsen the ammonia stripping problem. Carbon dioxide also is soluble in water and, when dissolved, forms carbonic acid and carbonates. This causes the water to become more acidic. This relatively acidic aqueous phase pulls the relatively-alkaline ammonia into it. In the process, ammonia molecules are removed or stripped from the gas phase and thus are unavailable for gas detection.

Many known ammonia gas sensors fail to address these ammonia-stripping concerns, or fail to properly account for them. Others seek to address them by completely removing the water in its entirety, i.e., both liquid-phase water and water vapor. Recognizing the general concerns of the stripping of breath ammonia by water, U.S. Pat. No. 4,947,861 (Hamilton), for example, teaches the use of a solid-state body of alkaline hygroscopic material, e.g., sodium hydroxide, to substantially remove water vapor from the breath, but while being inert to the ammonia in the presence of water, before the dehydrated sample is analyzed. Hamilton teaches countering the deleterious interaction of ammonia with water by removing as much water as possible before the sample is analyzed. According to Hamilton, the dehydrated breath sample should be "substantially free of water vapor." (Hamilton, e.g., col. 4, lines 1-2.)

To address and overcome such issues, in systems, apparatus and methods according to the present invention, the breath sample is conditioned so that it has a relative humidity that is controlled to facilitate or optimize the ability to sense the ammonia in the sample. With reference to FIG. 1, the breath sample as originally obtained from the patient (also referred to herein as the "original" breath sample) has an ammonia concentration $[NH_3]_o$ and water concentration $[H_2O]_o$. That original breath sample is inputted into a breath conditioning device, which conditions the original breath sample most importantly to ensure that the relative humidity is at a desired, predetermined level or within a desired range suitable for sensing. This conditioning yields a "conditioned" breath sample, wherein the ammonia gas in the original breath sample preferably is largely if not entirely retained, but wherein the relative humidity is reduced to the desired level or range. Because relative humidity is a function of temperature, and in view of the typical temperature differences between original breath samples and breath sensing devices, preferably the relative humidity of the original breath sample is reduced to the desired level at a temperature, or within a temperature range, of the internal components of the breath analysis system, and of its sensing system. The conditioned breath sample, which has an ammonia concentration $[NH_3]_c$ and water concentration $[H_2O]_c$, then serves as the input to an analysis or sensing device that senses the conditioned sample to determine the presence and preferably the amount or concentration of ammonia in it. An output or signal is then generated that provides information about the results of the sensing. In this way, the breath sample can be conditioned to reduce or eliminate interfering or otherwise deleterious effects, such as the ammonia-stripping effects described herein above.

Against the backdrop of this teaching, the present inventors have discovered that, contrary to the teaching of Hamilton and others, the sensing of breath ammonia can be enhanced and even optimized by intentionally having a certain amount of water vapor in the sample during the sensing. Indeed, it is acceptable or even desirable in some applications for the sample to include some level of aqueous condensate.

Figure 2:
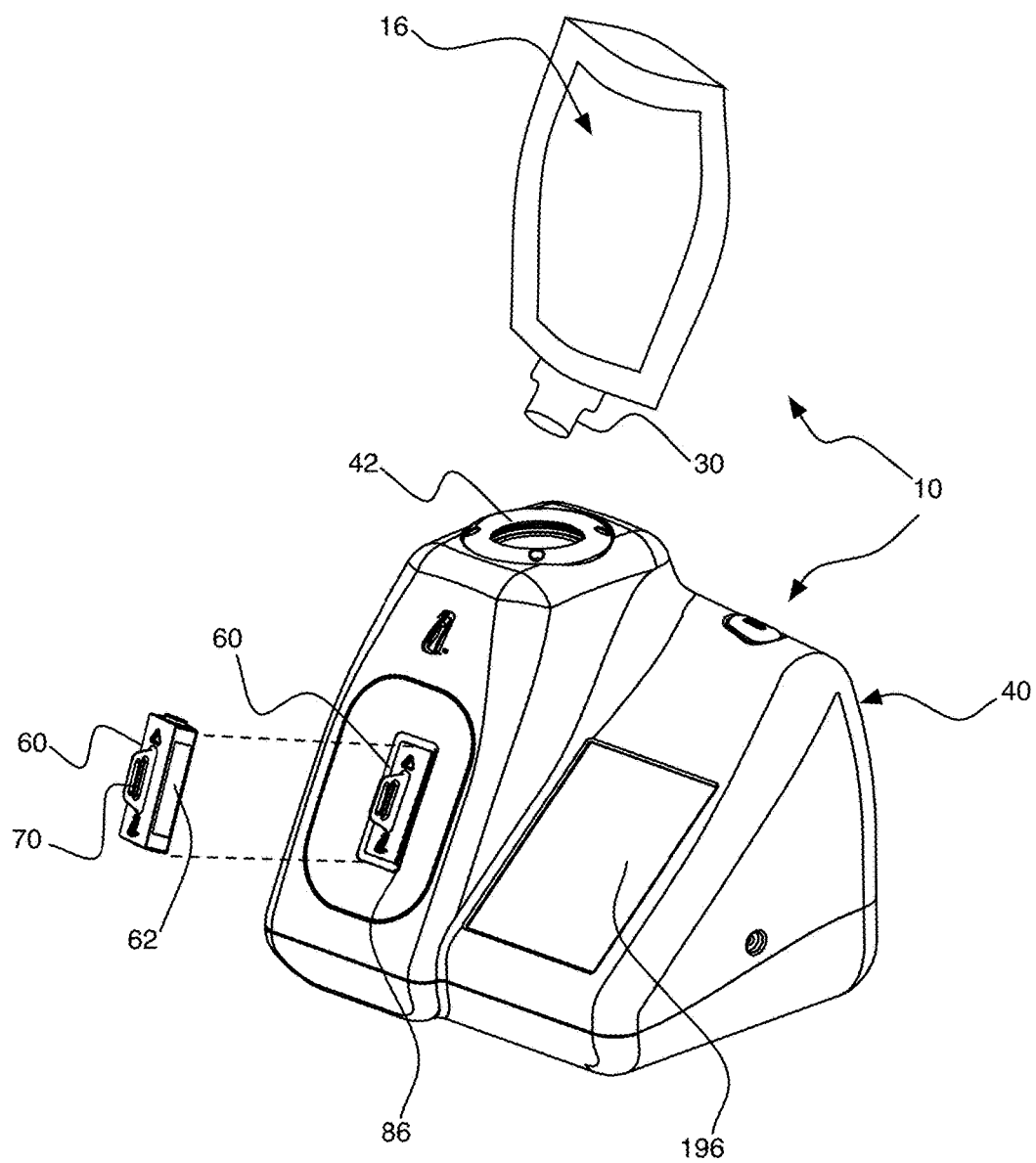
FIG. 2 is a perspective view of a breath analysis system according to a presently preferred embodiment of one aspect of the invention.
Figure 3:
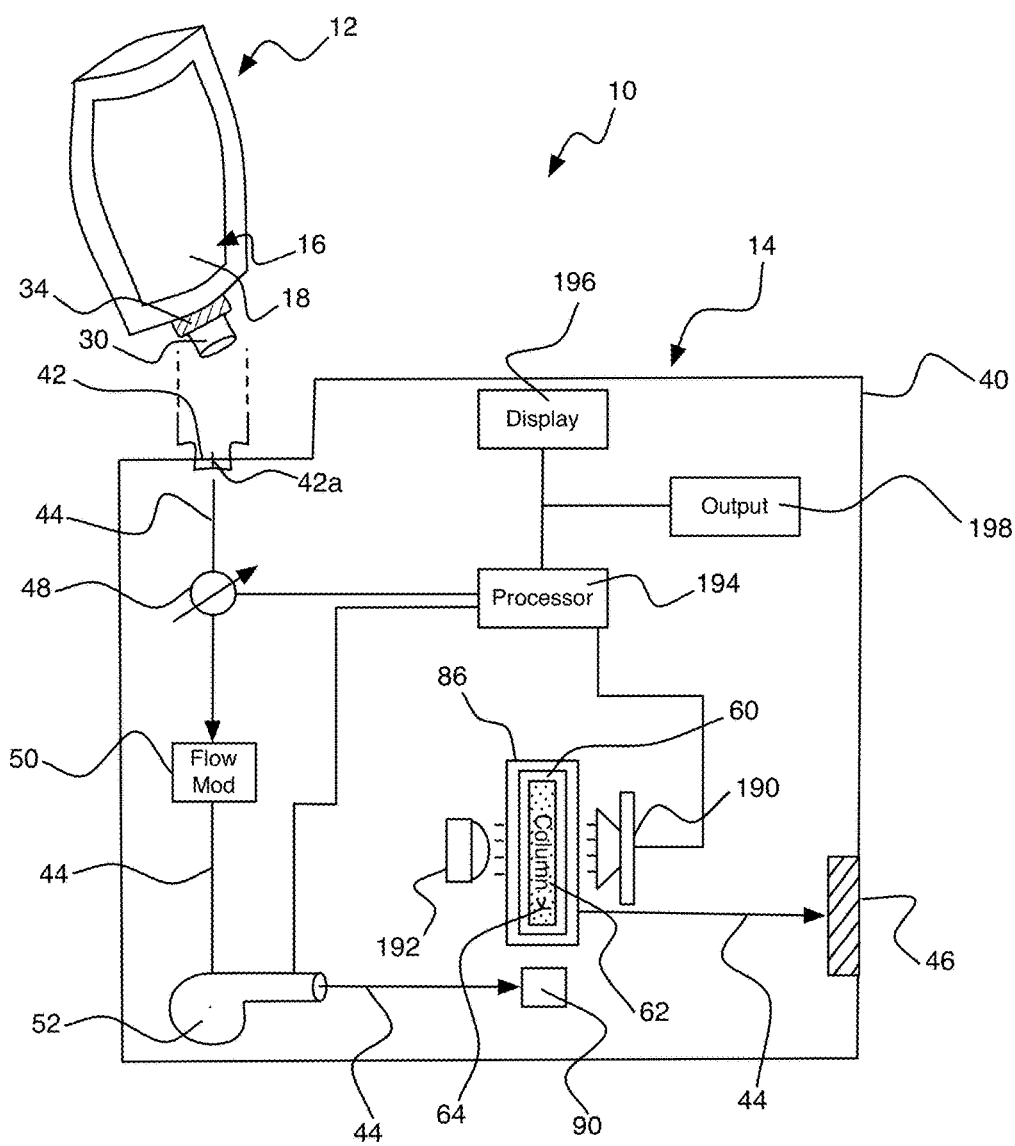
FIG. 3 is a functional block diagram of the breath analysis system shown in FIG. 2.

To illustrate various aspects of the invention, a breath sensing apparatus 10 for sensing ammonia in a breath sample according to a presently preferred embodiment of the invention will now be described. FIG. 2 shows a perspective view of the apparatus, and FIG. 3 provides a hardware block diagram of it. In this preferred embodiment, apparatus 10 is a portable device suitable for field use, or in the home of a patient or subject, and thus is not confined to use in a laboratory or hospital setting.

Apparatus 10 comprises a breath sample collection subsystem 12 and a breath sample sensing subsystem 14. Breath sample collection subsystem 12 and breath sample sensing subsystem 14 in this preferred but merely illustrative embodiment are physically separate, attachable and detachable components, but this is not necessarily required or limiting. Alternative configurations, e.g., in which the breath sample collection subsystem 12 and sensing subsystem 14 are contained in a single unit, are within the scope of the invention.

Although, as just noted, breath sample collection subsystem 12 may comprise a direct flow-through conduit to the sensing subsystem 14, in this embodiment it provides a means to retain or store the breath sample until it is ready for use in the breath sensing, and when called upon to do so, to deliver the breath sample to the sensing subsystem 14. The breath sample collection subsystem 12 may comprise a variety of forms, provided it can perform the basic functions required of it as described herein.

Figure 4:
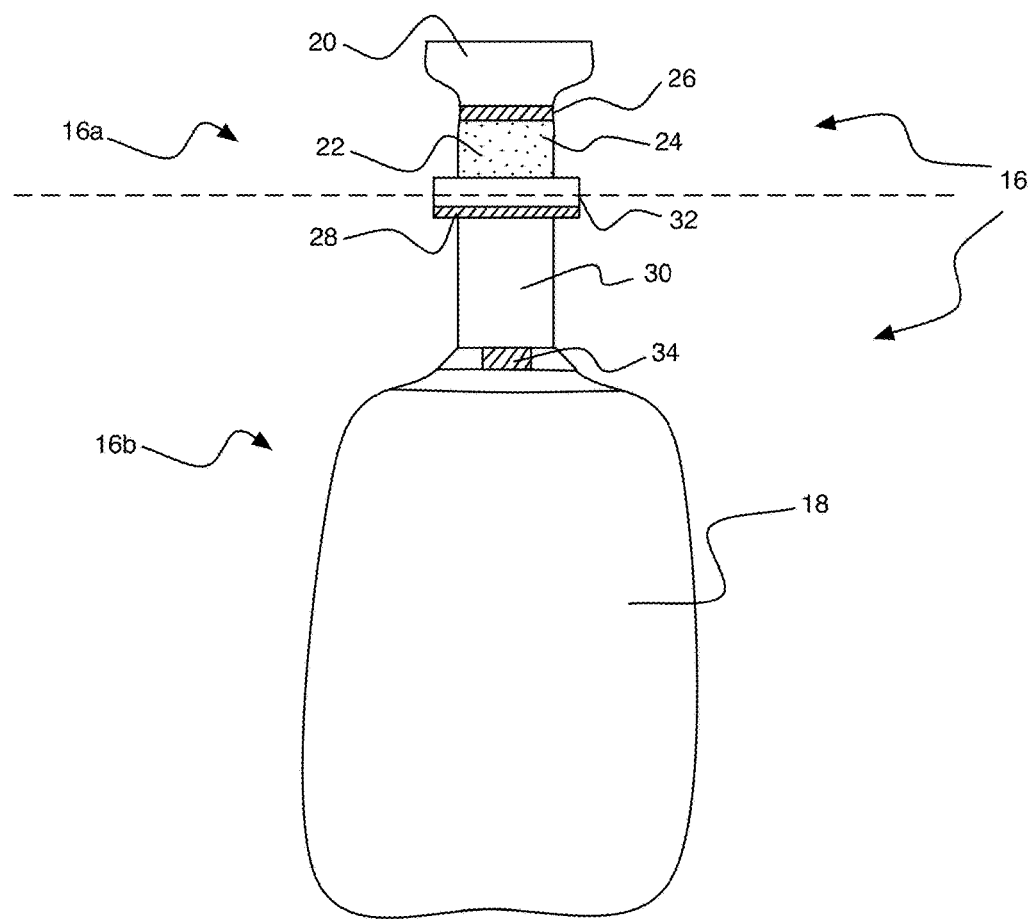
FIG. 4 shows a breath sample bag assembly used in the breath analysis system of FIG. 2 and FIG. 3.

In this embodiment, breath sample collection subsystem 12 comprises a breath sample bag assembly 16 for retention of a breath sample, and for delivery of the breath sample to the breath sample sensing subsystem 14 as further described herein below. Breath sample bag assembly 16 according to this embodiment, shown separately and enlarged in FIG. 4, comprises a detachable breath sample input unit 16a and a bag unit 16b, the latter comprising a breath bag 18.

The breath sample input unit 16a provides a means for inputting the breath sample into the bag unit 16b in a manner so that contamination or otherwise unwanted external gases or substances (external to the breath sample itself) are not allowed to infiltrate into the bag 18. Although a variety of breath sample inputs are possible, in presently preferred breath sample collection subsystem 12 the breath sample input unit 16a comprises a mouthpiece 20. Examples of alternative breath sample inputs would include tubular or conduit-based inputs, inputs that segregate the breath sample into components or segments, and the like.

Breath bag 18 comprises a flexible, air-tight bag that has insubstantial or no permeability for breath samples of the type for which this system is used. The permeability of ammonia out of or through the bag under storage or retention conditions should be zero or as close to zero as possible over anticipated or desired retention times and conditions. Any leakage should be below the lower range of detectability for the overall device so that it does not affect the sensing results. Examples of bags generally suitable for present uses in sensing ammonia include Tedlar® and Mylar® foil bags. (Tedlar® and Mylar® are registered trademarks of the E.I. Du Pont de Nemours & Co. of Wilmington, Del.) Breath bag 16 according to this embodiment comprises a Mylar® foil bag, which is generally preferred based on its relatively low permeability for ammonia. For applications involving transient analysis, other bag materials may be used, such as polyethylene.

The breath sample collection subsystem, and more specifically the breath sample input unit 16a in this embodiment, also includes a breath conditioning device that conditions the original breath sample so that it has a desired level or range of relatively humidity. In the presently preferred embodiment, the breath conditioning device comprises a pre-filter 22 in fluid communication with bag 18 between the bag itself and the mouthpiece 20 so that a breath sample inputted into the mouthpiece passes through pre-filter 22 and into the interior of the bag 18.

Pre-filter 22 comprises a granular desiccant 24. The grain size (including the grain size distribution) of desiccant 22 preferably is selected so that it is effective in reducing the relative humidity of the gas sample, and more preferably in reducing the total water content of the gas sample, but wherein the risk of inadvertent inhalation or ingestion of the desiccant by the patient or other user is minimized. This balancing takes into account the fact that larger particle sizes generally facilitate flow (reduce flow resistance) but decrease the total surface area available for interaction with and removal of the water. This latter potential impact in some instances can be mitigated, for example, by increasing the porosity or tortuosity of the grains or particles themselves. In view of these criteria, the granular desiccant 24 preferably has a mesh size of at least 4, and more preferably has a mesh size of between about 4 and about 100. Given the relative importance of accurate and reliable removal of the water to the desired levels, the desired mesh size preferably is at the lower end of the broader range, e.g., between about 5 and about 80, and more preferably between about 10 and about 30-40.

A method that is used to determine bead size is described. In a room with relative humidity in the range of 15 to 30% and at temperatures of 74° to 79° F., sieving takes place manually. A sample of beads is placed into a set of sieves, that are manufactured according to ASTM E-11 specifications. Sieve assemblies are shaken by hand, rotated, and repeatedly struck against the palm of the hand for some period of time, for example 5 to 15 minutes, or until no significant sieving appears to be ongoing. Weight or volume fractions are assessed. The major fraction is the fraction with the greatest volume or weight of material collected. Minor fractions are those with approximately less than 10% of the weight of the total sample. Moderate fractions are in between. Sieve sizes used in these fractionations may include: 35, 40, 50, 60, 70, 100, 120, 140, 170, and 200.

The desiccant material preferably is selected so that it does not extract ammonia from the breath sample, or does so only minimally. By this is meant that the desiccant 24 either does not extract any of the available ammonia, or that to the extent some ammonia is extracted, the amount is sufficiently below the sensing or measurement threshold so that the measurement of the ammonia in the breath sample analysis device is not adversely affected within its sensitivity range and margin of error. In general, alkaline desiccants do not extract ammonia, or do so only nominally. Preferred desiccants have alkalinity that is greater than that of ammonia. Examples of preferred desiccants include sodium hydroxide pellets, soda lime, and Ascarite II®, each of which generally does not extract ammonia. Various other alkaline desiccants suitable for use are known to those skilled in the art.

Given the granular nature of the desiccant and the fact that many desiccant materials suitable for the device from a functional perspective may be toxic to humans or otherwise pose an ingestion risk, screens 26 and 28 are disposed at respective flow ends of pre-filter 22.

The breath sample input unit 16a, and more specifically the mouthpiece 20, comes into direct contact with the patient, and therefore should not be re-used unless thoroughly disinfected. In addition, the pre-filter 22 traps or contains certain components of the breath sample, including water and potentially water-borne microorganisms or other contaminants, and similarly should not be re-used without thorough disinfection. Accordingly, in presently preferred embodiments, the detachable breath sample input unit 16a, comprising the mouthpiece 20 and pre-filter 22, is detachable and disposable.

The bag unit 16b in this embodiment is configured to receive and retain the breath sample during a breath sample "collection" mode, during which breath sample input unit 16a is attached. Bag unit 16b also is configured to provide that breath sample to the breath sample sensing subsystem 14 while unit 16b is detached from unit 16a during a breath sample "sensing" mode. A ferrule 30 is fixedly coupled to the end of bag 18 adjacent to pre-filter 22. Bag unit 16b, and more specifically ferrule 30, is detachably coupled to the breath sample input unit 16a, and more specifically to pre-filter 22, using a coupler 32. A one-way valve 34, which in this embodiment comprises a simple flapper valve, is disposed at the interface between ferrule 30 and the top interior of bag 18 so that breath blown into mouthpiece 20 and passing into bag 18 via pre-filter 22 and ferrule 30 is trapped in the bag interior and is not allowed to escape. These components are conjoined in air-tight fashion so that, when a patient blows breath into mouthpiece 20, the breath sample travels through pre-filter 22 and ferrule 30 and into the interior of bag 18 without leakage.

To reiterate and clarify, breath sample collection subsystem 12 comprises two primary and detachable components, i.e., breath sample input unit 16a and breath sample bag unit 16b. Input unit 16a comprises mouthpiece 20 and pre-filter 22 fixedly coupled to one another. Bag unit 16b comprises bag 18 with fixedly-coupled ferrule 30. These two components 16a and 16b are detachably coupled to one another by coupler 32 during the breath sample collection mode. When detached, bag unit 16b can be used with the breath sample sensing subsystem 14 as described herein below to perform in the sensing mode. The input unit 16a, having been directly contacted by the patient, is disposable and can be discarded.

Turning to the breath sample sensing subsystem 14, and with reference to FIG. 3, it comprises a base 40 (also shown in FIG. 2) that houses its various components as described more fully herein below. An input port 42 is provided at the top of base 40 for receiving the distal end of ferrule 30 and thereby forming an air-tight seal between the interior of bag 18 and an interior flow path 44 of base 40. A post or stanchion 42a is disposed in port 42 to interact with and open one-way valve 34 in bag unit 16b so that the breath sample in bag 18 is allowed to flow into flow path 44. Flow path 44 begins at input port 42 and extends through base 40, as described more fully herein below, to and outwardly from an exhaust port 46. For directional reference, flow, movement or corresponding relative positioning along the flow path 44 in the direction from input port 42 and toward exhaust port 46 is referred to herein as "downstream," and flow, movement or positioning in the opposite direction, from exhaust port 46 toward input port 42, is referred to herein as "upstream."

It is useful and in most cases important to quantitatively measure certain flow characteristics of the conditioned breath sample within flow path 44. Examples of such flow characteristics include flow velocity, flow rate (mass or volumetric), and the like. Accordingly, in this embodiment a flow meter 48 is positioned in flow path 44 downstream from input port 42. Flow meter 48 measures flow velocity and flow volume of the breath sample at that location.

Breath sample sensing subsystem 14 further includes a flow modulator in the form of a flow restrictor 50 downstream from flow meter 38, and a pump 52 downstream from flow restrictor 50, both within flow path 44. Pump 52 is appropriately sized and powered so that it is suitable for drawing the conditioned breath sample from bag 18 and causing the breath sample to flow through the flow path 44 and out exhaust port 46, taking into account the full system configuration as described herein. Pump 52 is selected and operated to move the conditioned breath sample through flow path 44, including the full extent of its components as described herein, while maintaining the flow rate at a desired level or within a desired range. In apparatus 10, a typical breath sample would comprise approximately 400 to 450 milliliters ("ml.") of gas, and apparatus 10 would be configured to pass this entire volume of gas through flow path 44 in about 3 minutes, so that the average flow rate is about 100-150 ml./min. It may be noted that, in some applications, one may withdraw the breath sample from the bag to the point at which all of the gas has been evacuated and a small vacuum is drawn to ensure that all of the breath sample has been analyzed.

It is characteristic of many pumps to provide a periodically-varying or pulsating pressure or flow rate attributable to the internal operation of the pump. This can cause undesirable effects, such as local condensation, adverse effects on reaction kinetics, and the like. In many applications, and particularly those such as ammonia sensing in which the presence of water or other condensate is deleterious to system operation, it is desirable to smooth the flow, avoid pressure transients, to provide a relative steady, modest pressure drop down the flow path, and to minimize unwanted flow or pressure variations. In apparatus 10, for example, flow restrictor 50 functions to absorb and smooth perturbations created by pump 52.

Breath sample sensing subsystem 14 further comprises a sensor or sensing subsystem that analyzes the conditioned breath sample and senses the presence, preferably including the concentration or amount, of ammonia in the sample.

Apparatus 10 senses ammonia using colorimetric principles. More specifically, it is designed so that any ammonia in the breath sample is caused to react with one or more components of the system referred to herein as the interactant, whereupon the reaction gives rise to a change in one or more optical characteristics of the system or some component of it in a way that provides information about the presence, concentration or amount of the ammonia in the breath sample. "React" and "reaction" as the terms are used herein include not only chemical (i.e., ionic or covalent bonding) reactions, but other forms of reaction in which the state of the analyte and/or analyte interactant, their properties or state, or the properties or state of their environment is changed. Examples of reaction regimes might include, for example, physical or chemical absorption or adsorption, physical or chemical reaction, Van der Waals interactions, hydrogen bonding, electrostatic bonding, transitions that absorb or release thermal energy, and the like. The reaction may be any interaction that brings about the optical characteristic or characteristics. The change in the optical characteristic or characteristics may be brought about in or at any component or area of the apparatus, but in presently preferred embodiments and method implementations the optical change occurs in the reaction zone. In apparatus 10, this reaction zone initially comprises the interactant. As the apparatus is operated in the sensing mode, the conditioned breath sample, presumably containing ammonia, is passed through this reaction zone so that the ammonia contacts and reacts with the interactant, whereupon the optical change occurs in components of this reaction zone in relation to the amount of the ammonia in the breath sample. As the ammonia reacts with the interactant, the contents of the reaction zone undergo an optical change relative to its initial or "reference" optical conditions. Apparatus 10 is designed so that the desired information about the ammonia, e.g., its presence and its amount or concentration, is embodied in the optical change.

Optical characteristics that can be used in connection with this aspect of the invention comprise any optical measurement that is subject to change in relation to a change in the presence of ammonia, or in relation to the concentration of the ammonia. Examples include the color, colors or spectral composition of the reaction zone, the intensity of the radiation at a particular frequency, frequency band, range of frequencies, reflectance, absorbance, fluorescence, and others. The sensing subsystem is designed and configured to sense this optical change relative to the reference and to generate an output representative of this change in the optical characteristic or characteristics.

Figure 5:
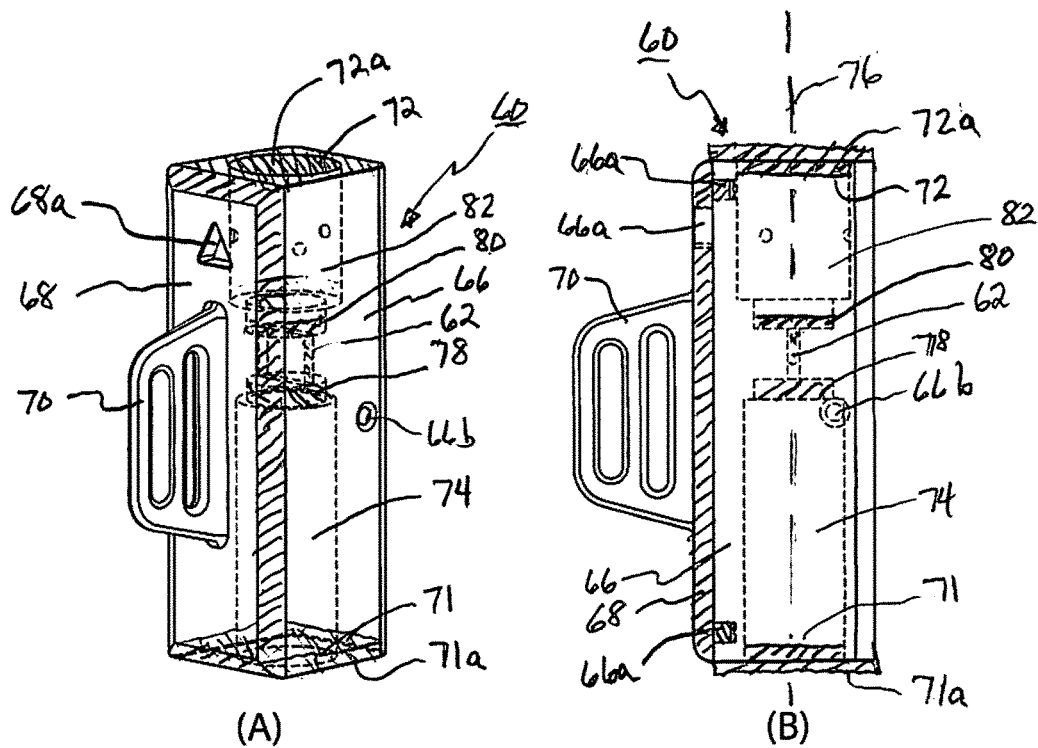
FIG. 5 shows a cartridge and associated column used in the breath analysis system of FIG. 2 and FIG. 3.
Figure 5:
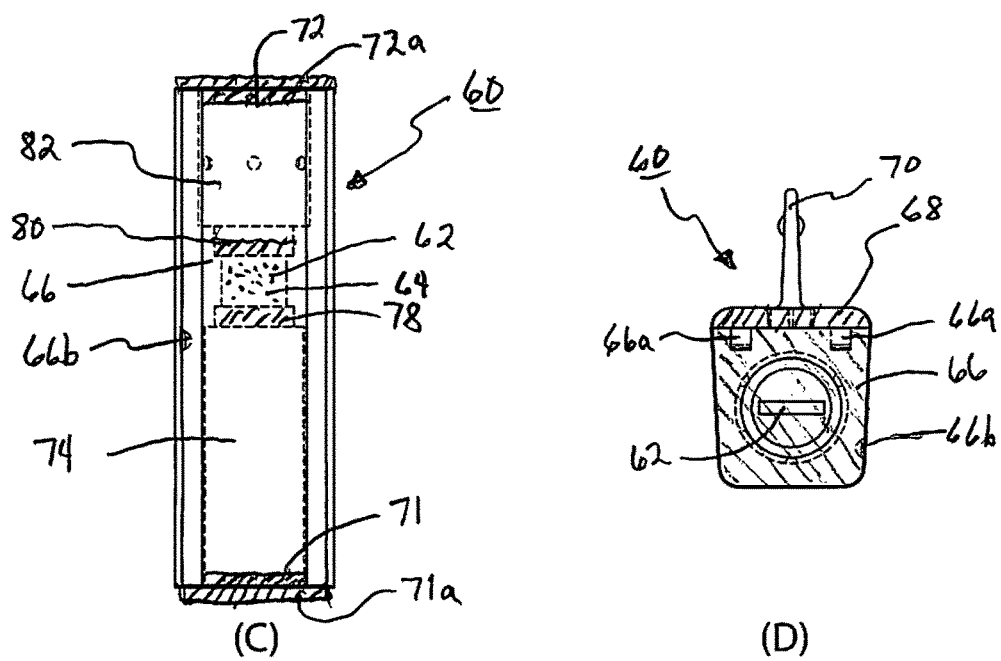

As embodied in apparatus 10, the sensing subsystem of breath sample sensing subsystem 14 comprises a detachable cartridge 60 sized and configured to be inserted into and mate with base in substantially light-tight or light-sealing form. With reference to FIG. 5, FIG. 5A shows a perspective view of cartridge 60, FIG. 5B shows a side view, FIG. 5C shows a back view, and FIG. 5D shows a top view. As shown in the drawings, cartridge 60 comprises a column 62 that comprises the reaction zone. Column 62 contains an interactant 64, as described more fully herein below. Column 62 is disposed in an optically-transparent housing 66, for example, which may comprise an injection-molded polymer, such as an acrylic or acrylic resin, a polycarbonate, a polyethylene terephthalate, a polystyrene, a styrene-butadiene, or the like. Housing 66 is fixedly coupled to a light-opaque backing plate 68 by a set of mounting and aligning pins 66a. A handle 70 is rigidly coupled to the backing plate 68. A small window 68a is provided in backing plate 68 so that, when the illuminator (described herein below) is operating, a user can see its light through window 68b to indicate a powered-up state. A concavity or detent 66b is provided in the external surface of body 66 to facilitate retention of the cartridge 60 in base 40 when the cartridge is inserted.

Housing 66 has an inlet 70 and an outlet 72. Each is covered and sealed by a foil laminate, 70a and 72a, respectively, comprising a thin layer of metal foil sandwiched between two layers of thermoplastic material. Contiguously with and immediately downstream of inlet 70 is a substantially-cylindrical cavity 74 centered about the longitudinal axis 76 of the cartridge 60. (Note that in FIG. 5A-C, the downstream direction, in which the breath sample flows, is upward.) A porous polyethylene disk 78 is disposed at the downstream end of cavity 74 and at the upstream base of column 62. Similarly, another porous polyethylene disk 80 is disposed at the downstream end of column 62.

Column 62 comprises a cuboidal space or cavity (having a rectangular cross section in a plane normal to the flow path through the cartridge) centered longitudinally within cartridge housing 66. This can perhaps best be seen in FIG. 5D, which shows a top view of cartridge 60, but wherein column 62 is shown through the seal.

An upper cavity or well 82 is disposed downstream from disk 80, which well 82 is sealed at its opposite or downstream end by seal 72b.

As shown, for example, in FIG. 2, cartridge 60 is configured to be inserted into a rectangular aperture 72 disposed in the front exterior surface of base 40 and to When a user wishes to use apparatus 10 to perform a test for ammonia, the user grips cartridge 60 using handle 70.

Base 40 comprises a cartridge receiver 86 for detachably receiving cartridge 60, as shown, for example, in FIG. 2, thereby detachably mating it with the base 40 in substantially light-tight or light-sealing form. Under normal conditions of non-use, i.e., when cartridge 60 is not inserted into aperture 72 and base 40 is not operatively in sensing mode, the aperture in base 40 that comprises receiver 86 is covered or blocked by a moveable door (not shown in the drawing) that is substantially conformal with the front exterior surface of base 40 when the door is in its closed position. The door is spring-loaded or otherwise elastically biased so that it is normally closed, but gives way and moves inwardly to an open position when the cartridge 60 is pressed against it and a small or slight force is applied to insert the cartridge. When cartridge 60 is inserted into receiver 86, it is positioned by the respective geometries of the receiver 86 and cartridge housing 66 so that the longitudinal cartridge flow path from cartridge inlet 70, through column 62 and to outlet 72, is in fluid communication with and becomes part of flow path 44 in base 40.

Figure 6:
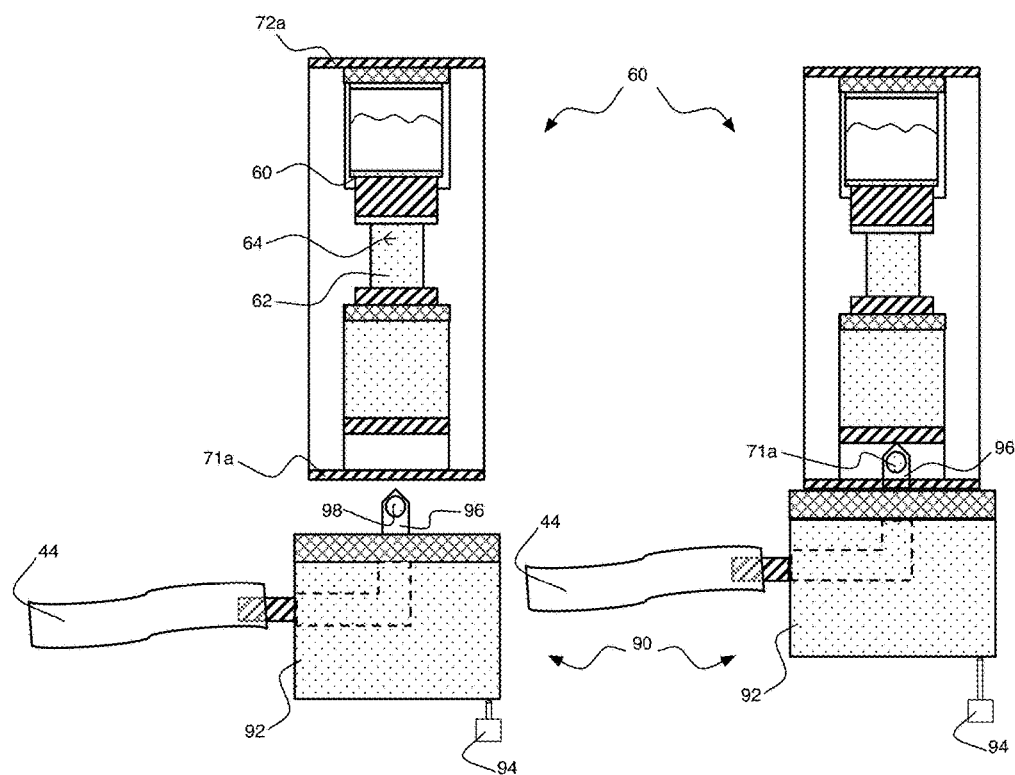
FIG. 6 is a cartridge embodiment.

As the cartridge 60 is inserted into receiver 86, or after such insertion and at the appropriate time, cartridge 60 is physically coupled to the flow path 44 in base 40 as follows. With reference to FIG. 6, base 40 includes a seal piercing assembly 90. Assembly 90 comprises a block 92 that is coupled to a moveable actuator 94. Assembly 90 also comprises a needle 96 that includes a fluid channel 98 fluidically coupled to the breath sample, e.g., from the flow path 44 of base 40 in FIG. 3. In its normal state prior to sensing mode, block 92 is spaced from the cartridge 60.

In preparation for the breath sample sensing mode, the user affixes bag unit 16b to base 40 at input port 42, and stanchion 42a opens one-way valve 34 so that the breath sample in bag 18 is in fluid communication with flow path 44 of base 40. The user also places cartridge 60 in receiver 86 of base 40.

When the breath sample sensing mode begins, pump 52 is engaged to begin the flow of the breath sample from bag 18 into the flow channel. Actuator 94 moves block 92 to the inlet 70 of cartridge 60, and needle 96 is inserted through sealing layer 72a so that the flow path through cartridge 60 is opened and the breath sample flows through flow path 44 and into the cartridge flow path. More specifically, the breath sample is actively flowed through flow path 44 and into column and reaction zone 62, where the ammonia in the sample, (presuming ammonia is present in it), contacts and reacts with the interactant to bring about the change in optical characteristic or characteristics.

Figure 7:
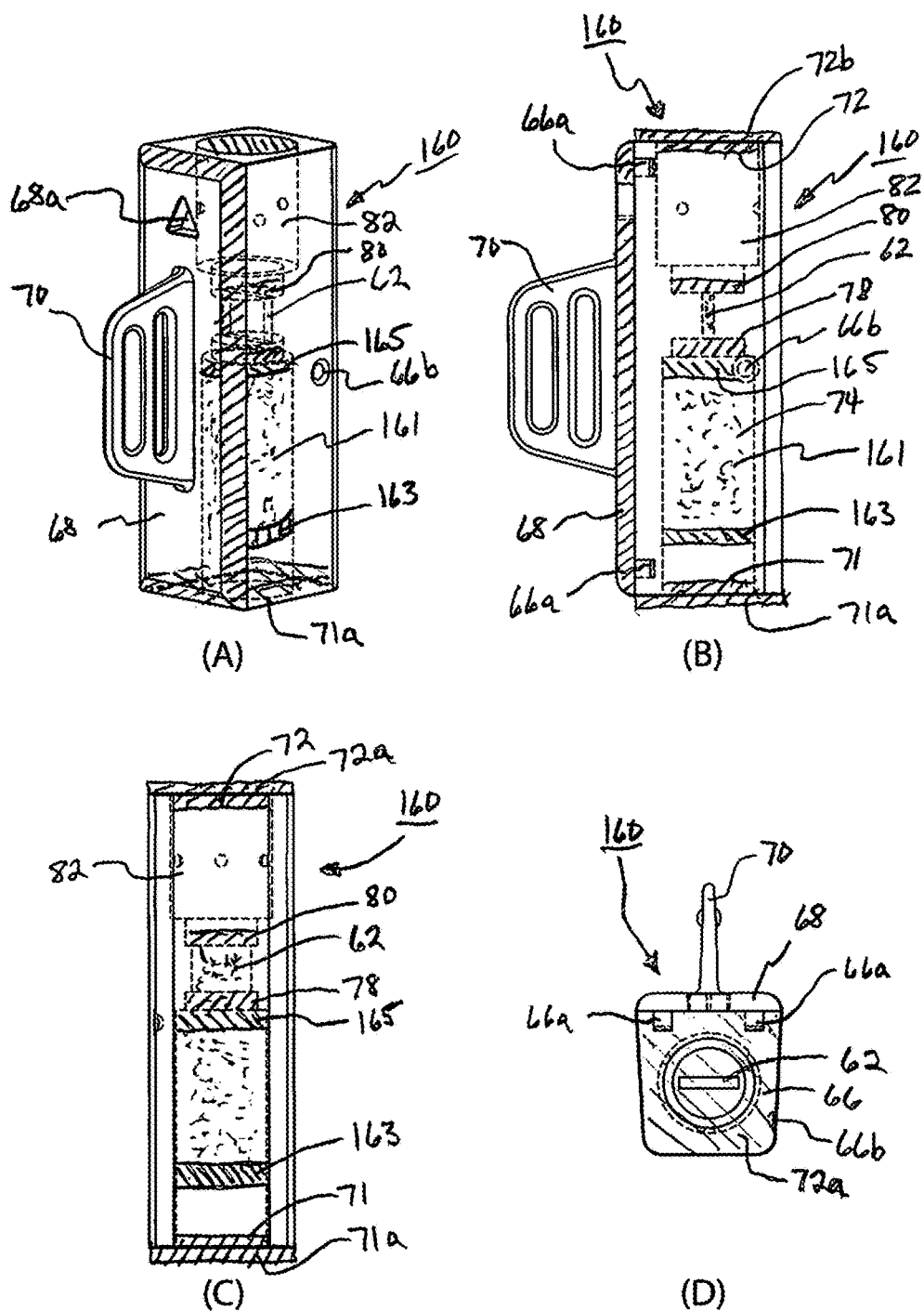
FIG. 7 is an alternative embodiment of a cartridge.

An alternative embodiment, and with reference to FIG. 7, a cartridge 160 is provided which is virtually identical to cartridge 60, but wherein a fluid conditioner, in this case a secondary desiccant, is provided. Most of the components of cartridge 160 are the same as those in cartridge 60, and accordingly the same reference numerals and characters apply and are used in FIG. 7 to refer to them. As noted, cartridge 160 differs from cartridge 60 in that cartridge 160 comprises a fluid conditioner in the form of a secondary desiccant. More specifically, in cartridge 160, a flow conditioner 161 is disposed in cylindrical cavity 74, immediately upstream from column 62. A porous polyethylene disk 163 is disposed in cavity 74 adjacent to but spaced from cartridge inlet 70. At the top or downstream edge of cavity 74, a fibrous polyethylene disk 165 is disposed immediately adjacent to disk 78, so that lower disk 163 and upper disk 165 form the linear bounds of flow conditioner. A granular desiccant material 167 suitable for further desiccation of the conditioned breath sample, e.g., such as those described herein above, is disposed in flow conditioner 161 so that, as the conditioned breath sample flows through flow path 44 and through cartridge 160, the gas is further conditioned with the desiccant to remove water as desired, and as further described herein. Cartridge 161 may be used in base 40 as described herein above with respect to cartridge 60. It may be disposed in base 40 at receiver 86, and engaged by seal piercing assembly 90 as described herein above as well.

In the preferred cartridge embodiments shown in FIG. 5 and FIG. 6, the interactant is disposed in column 62, which also serves as the reaction zone. It should be noted, however, that although this generally is preferred, other configurations in which the interactant is initially separate from the reaction zone are possible. Interactant 64, for example, may be predisposed in upper cavity 82 above column 62, so that, during the sensing mode, the interactant is transferred, e.g., by gravity, gas pressure or the like, into column 62 and reaction occurs there. Alternatively, interactant 64 may be predisposed in cavity 74 and, during the sensing mode, the flow of the breath sample gas in flow path 44 entrains the interactant and thereby moves it, or a portion of it, up into column 62 where the ammonia can react with the interactant.

In presently preferred embodiments and method implementations according to the invention, the interactant 64 comprises an ammonia-reactive indicator, preferably a pH indicator, coupled to a substrate, wherein the ammonia-reactive indicator has a pKa of less than 8. The indicator may comprise a material that is specifically reactive with ammonia, or ammonium ions. Under most applications involving human breath, however, including a range of pathophysiological states of interest in this context, ammonia and ammonium ions are likely to be the only substantially alkaline constituents in breath. Accordingly, one generally may use a pH indicator, particularly one that is most responsive, or selectively responsive at pH ranges well into the alkaline range, as the interactant, and one need not require a material that is specifically selective for ammonia.

The interactant is configured to interact with the ammonia in the breath sample to yield a "product" (e.g., a reaction product or resultant composition) and to cause a change in an optical characteristic between the interactant and the product in relation to the amount of the ammonia that interacts with the interactant. The ammonia-reactive indicator and the substrate are disposed in the interactant region that is configured to receive the breath sample. Note that the term "react" as used herein is used in its broad sense, and can include not only chemical reactions involving covalent or ionic bonding, but also other forms of interaction, e.g., such as complexing, chelation, physical interactions such as Van der Wals bonding, and the like.

In presently preferred embodiments and method implementations of the present invention, it is desirable to use a small disposable ammonia cartridge such as cartridge 60 for personal, regular (e.g., daily) use in a clinical or home. Large consumables (namely the interactant) are inconvenient and relatively more expensive. To reduce the size of the consumable and that of the overall device required to analyze ammonia, a smaller particle size for the interactant generally is preferred.

Although the interactant may be made using a variety of techniques, a presently preferred method for making interactant 64 will now be described.

Figure 8:
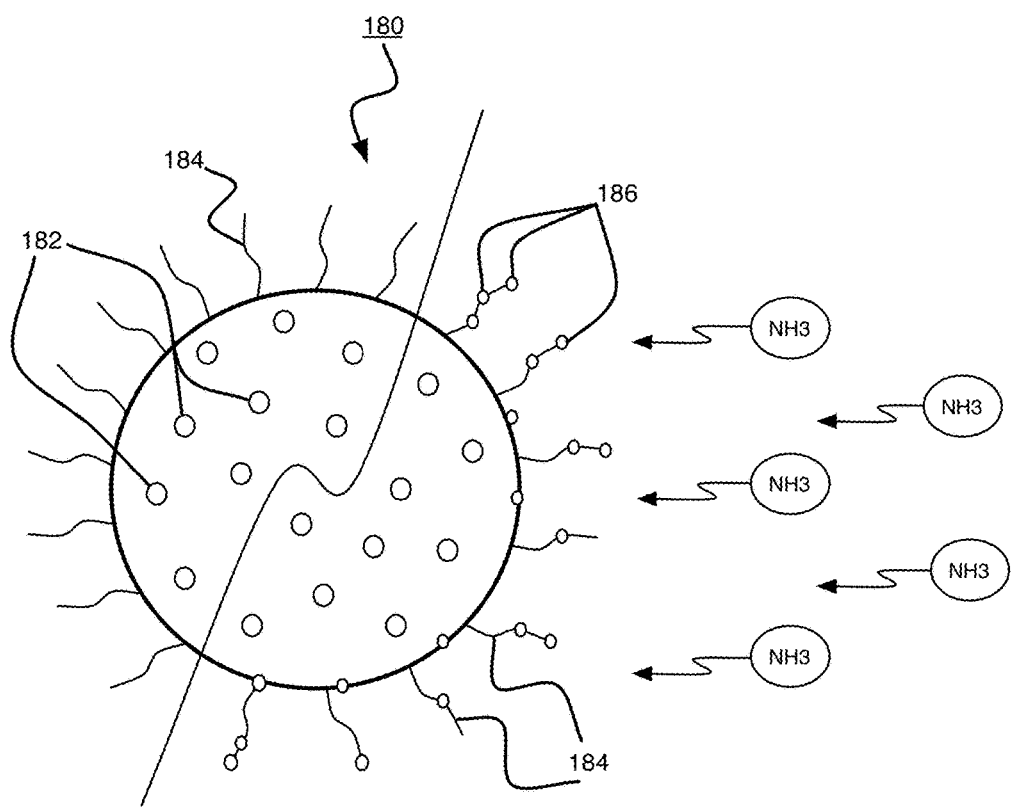
FIG. 8 shows a schematic view of a substrate with an ammonia-reactive indicator coupled to the substrate surface, a plurality of which substrates being contained in the column of FIG. 5.

Interactant 64 comprises a plurality of substrates or supports. Although in general they may take the form of fibers, particles, pores, etc., in this embodiment they comprise silica gel beads. Silica gel is advantageous because it has a very high adsorption efficiency for ammonia. One such bead 180, as an example, is shown in FIG. 8. The size of the support substrate depends on such factors as the breath sample flow rate, device geometry, and desired detection limit. Commercial gas tubes for measurement of ammonia in ambient air use relatively large particles with a mesh size typically between about 5 and about 30, depending on the manufacturer. The larger particles have a lower extraction efficiency, allowing the ammonia to penetrate a column of the beads up to several inches long, provided the length of color formation is satisfactory. In preferred embodiments, the support substrates (here silica gel beads 180) preferably have a mesh size of between 20 and 200. Substrate particles sizes of between about 200 mesh and about 5 mesh, or more preferably between about 100 and about 20 mesh, are particularly desired. Beads 180 also have pores 182 that provide additional surface area. The pores preferably are sized so that they provide useful surface area for interaction with the dye and with the ammonia. Good results have been obtained using 35 to 60 mesh silica gel beads with 60 angstrom pore size.

The ammonia-reactive indicator or pH indicator, designated in FIG. 8 by reference numeral 184, is coupled to the surface of bead 180. The pH indicator 84 may be adhered to the surface of the substrate 80 via any one or combination of adherence mechanisms, e.g., such as covalent bonding, ionic bonding, physical or physiochemical bonding, electrostatic bonding, adsorption, and the like. Preferably, the substrate and indicator are immersed in a solvent bath where the coupling can occur. Various solvents can be used for preparing and suspending the ammonia-reactive indicator. Examples include, but are not limited to, water, alcohols (e.g. methanol, ethanol, propanol, etc.), aprotic polar solvents (e.g., dimethylsulfoxide, dimethylformamide, etc.) and others. In some embodiments, a solvent is chosen that allows easy evaporation, such as a volatile alcohol (e.g., methanol, ethanol, propanol and/or other alcohols with a boiling point of less than 100° C.).

The amount of ammonia-reactive indicator (dye) that can be solvated is limited by the solubility of the dye in a given solvent. In a preferred method implementation according to this aspect of the invention, 50 mg of bromophenol blue is added to 50 milliliters ("mL") of isopropanol to prepare a 1 mg/mL solution and is agitated for 1 hour prior to use. Agitation can include high speed vortexing or gently rocking on an orbital rocker.

In the presently preferred embodiment and method implementation, the ammonia-reactive indicator 64 and/or the substrate 80, and preferably both, are contacted with an acid having at least two available protons to form the interactant 64. This protonation is illustrated in FIG. 8 by the protons 186 at the right portion of the drawing figure. The pKa for the dissociation of a first one of the protons is less than the pKa of the ammonia-reactive indicator. The boiling point of the acid in a 99% pure form is greater than 37° C. at standard atmospheric pressure.

Although the sequence of steps taken to adhere the pH indicator and protonate the material or materials is not necessarily limiting, in presently preferred implementations of the method the pH indicator is first adhered to the support substrate, and the combined materials are contacted with the acid or acids to simultaneously protonate them. Although not necessarily required or limiting, and although not wishing to be bound to any particular theory or phenomenology, it is preferable that the protonation occur not only at and on the pH indicator, but on the surface of the substrate as well.

The acidification or protonation of the ammonia-reactive indicator and support substrate can be a very important factor in preparing the interactant. To improve the extraction efficiency, the type of acid, the quantity and concentration of acid, the type of substrate particle, and the size of the particle all must be considered.

Many acids are known to those skilled in the art, such as hydrochloric acid, acetic acid, phosphoric acid, sulfuric acid and others. As noted herein above, the acid can be added to the material, to the solvated dye, or can be added to the finished product. In some embodiments, a fuming acid is preferred or otherwise can be used to protonate the dye-coated or impregnated substrate material. Preferably, the acid is a relatively strong one with a pKa less than the pKa of the base-sensitive dye. The concentrated acid preferably is relatively nonvolatile, with a preferred boiling temperature higher than 37° C. at 1 atmosphere ("atm"). Volatile acids are generally less stable in aging studies. In the presently preferred embodiments and method implementations as described herein, the acid is sulfuric acid. It has a pKa of −3 for the dissociation of the first proton and 1.99 for the second proton, and has a boiling point of 37° C.

A concentrated acid may be used in manufacturing the interactant. Such use of concentrated acid can be preferably, e.g., because it adds less water to the reaction, thereby reducing the required drying time and the potential loss of protons during drying.

The amount of acid to add is important, and can be critical, for the sensitivity of the base-sensitive pH indicator material. To maximize sensitivity, it is desirable to use the least amount of acid necessary to completely protonate the pH indicator dye as indicated by the color change (e.g., from blue to yellow for bromophenol blue) or other optical characteristic change. The amount of acid required to make this transition depends on several factors, such as type of material, size of material and pore size of the material. For example, neither polystyrene nor Teflon require any addition of acid for the bromophenol blue to take on its characteristic yellow hue. Silica gel, however, is relatively basic and turns the bromophenol blue a deep blue. For 100 milligrams ("mg") of 35- to 60-mesh silica with a 60 angstrom average or mean pore size, 10 microliters ("uL") of 0.1N HCl in 200 uL of dye/propanol solution is sufficient to turn the bromophenol blue to a yellow color. An incubation time of about 10 minutes at room temperature is required to allow the protons to diffuse throughout the silica gel and turn the bromophenol blue back to a yellow color. Diffusion of the protons continues during the drying procedure. 20 uL of 0.1N HCl has faster kinetics, but lower sensitivity in the finished product. 5 uL of 0.1N HCl does not allow for the dye to return to its yellow color. Lower quantities of 6 to 9 uL 0.1N HCl could potentially be used.

After the acidification or protonation is completed, the interactant material preferably is dried to remove the solvent. The drying method used can assist with diffusion and can be important for making a homogenous, consistent finished product. Examples of drying methods include allowing the beads to sit at room temperature, heating the beads, placing the beads under vacuum, and others, as well as combinations of such methods. Heating the beads improves diffusion and shortens drying time. Evaporation of the solvent, however, can create an uneven coating of the dye on the beads. Also, excessive heating can remove protons, gradually leading to a color shift back to blue/purple. The exact length of time that the beads should be heated is specific to such factors as the quantity of beads, the solvent and the acid.

In an illustrative preferred method, 1 gram ("g") of beads in 2 mL of 1 mg/mL bromophenol blue in propanol with 10 uL 1 N H2SO4 are heated for 45 min. at 80° C. (actual temperature, which can be different from the digital setpoint) in a 50 mL conical tube and then dried by heating at 110° C. for 30 min. or until no more condensation appears on a lid held at room temperature. The lack of condensation indicates that the majority of propanol and water have been evaporated and the beads are sufficiently dry for long term storage.

As noted herein above, for certain applications, it is generally preferable to leave some humidity on the substrate or interactant (e.g., by decreasing the drying time or temperature) to aid in the extraction of the ammonia and to create darker or more intense color changes at low ammonia concentrations. Removing the majority of the water content also may, for certain applications, be important for stability of the reagent at room temperature over time.

The use of silica gel is generally recommended as a substrate, e.g., because it allows for the extraction of water in addition to ammonia. As it extracts residual humidity in the breath sample, it increases the extraction efficiency of ammonia. This produces a result (e.g., high extraction efficiency and large color change) similar to leaving the beads slightly damp, but with the benefit of the stability of dry beads. Other hydrophilic materials with the potential for adsorbing residual humidity in the breath samples could also produce a similar result.

Incidentally, the manner in which the interactant is stored can be important for its stability over time. The interactant ideally should be aliquoted and stored in a gas-tight package shortly after manufacture. In the absence of a gas-tight seal, then it may be stored refrigerated or frozen in a closed container. The interactant preferably is used shortly after its manufacture, so that the need for special storage conditions are minimized or eliminated.

Further in accordance with this aspect of the invention, the apparatus comprises a sensing subsystem that senses the change in the optical characteristic and outputs a signal representative of the change in the optical characteristic. As embodied in apparatus 10, and with reference to FIG. 3, the sensing subsystem comprises a camera 190, preferably a digital camera, with an associated illuminating device 192, that can obtain optical characteristics, and changes in optical characteristics, of reaction zone 62. Illuminator 192 is disposed to provide light or an appropriate electromagnetic radiation at or through the reaction zone 64 in a manner so that the radiation interacts with the contents of the reaction zone and is then directed to camera 190. The light or electromagnetic radiation may comprise essentially a single frequency (a single, narrow band), a set of such single frequencies, on or more frequency ranges, or the like. In presently preferred apparatus 10, illuminator 192 provides white or broad-band light at a fixed level of intensity. (See arrows in FIG. 3 at illuminator 192.)

Digital camera 190 generates a signal that embodies the optical information on the optical characteristic or characteristics of interest. Signal generation can be accomplished using a wide variety of known transduction techniques. Commercially-available digital cameras, for example, typically provide automatic download of digital images as they are obtained, or transmit timed or framed video signals.

Apparatus 10 further comprises a processor 194 disposed within the interior of base 40 and operatively coupled to digital camera 190 to receive the signal from it. Processor 194 in this embodiment comprises a commercially-available general-purpose microprocessor or microcontroller appropriately configured and programmed to carry out the functions as described herein, in addition to standard housekeeping, testing and other functions known to those in the art. A power supply (not shown) is disposed in base 40 and is operatively coupled to processor 192 and the sensor components to provide necessary power to those devices.

In an alternative embodiment, the camera may be substituted with one or more photodetectors or the like, e.g., to reduce size and costs.

Apparatus 10 may output the information gleaned from the breath sensing using any one or combination of output forms or formats. In this specific embodiment, apparatus 10 comprises a touch screen display 196 disposed at the exterior of base 40 and operatively coupled to processor 194. Processor 194 is configured and programmed to present options, commands, instructions and the like on touch screen display 196, and to read and respond to touch commands received on it as they are received from the user. Processor 194 also outputs the sensed information to the user, e.g., in the form of a concentration of ammonia in the breath sample. This is not, however, limiting. The output also, or otherwise, may comprise a wired or, more preferably, a wireless data link or communications subsystem 198 with another device, such as a centralized database from which a care giver, such as a physician, family member, watch service or the like can monitor the output.

Another aspect of the invention, as noted herein above, involves a method for sensing ammonia in a breath sample. To more fully describe and illustrate this method, a presently preferred implementation of it will now be described with respect to the preferred but merely illustrative embodiment identified herein as apparatus 10. It should be noted and appreciated, however, that the method according to this aspect is not limited to this specific apparatus, and may be practiced or implemented with other hardware configurations. The actual hardware configurations of apparatus 10 also are illustrative, and may be modified in their details to facilitate such factors or objectives as miniaturization, efficacy, efficiency, manufacturability, cost, and the like.

The preferred method begins with a breath sample collection mode, in which the user provides a bag assembly 16 to the patient and has the patient exhale a breath sample through mouthpiece 20. This causes the conditioned breath sample to flow into bag 18, where it is retained by one-way valve 34.

In the process of carrying out this aspect of the method, pre-filter 22 conditions the original breath sample by reducing the water content, and particularly the relative humidity, to within a desired, pre-determined range. This desired range is an important feature of the method, and is discussed in further detail herein below. The range can be achieved, for example, by the design of pre-filter 22 as explained herein, alone or in combination with a secondary conditioner such as flow conditioner 161 as illustrated in FIG. 7. The preferred ranges and techniques for selecting them are further described herein below.

The user then takes the bag assembly 16, removes the mouthpiece and pre-filter assembly 16a, and inserts the bag unit 16b into the input port 42 of base 40 so that ferrule 30 firmly seats in the port 42.

Figure 9:
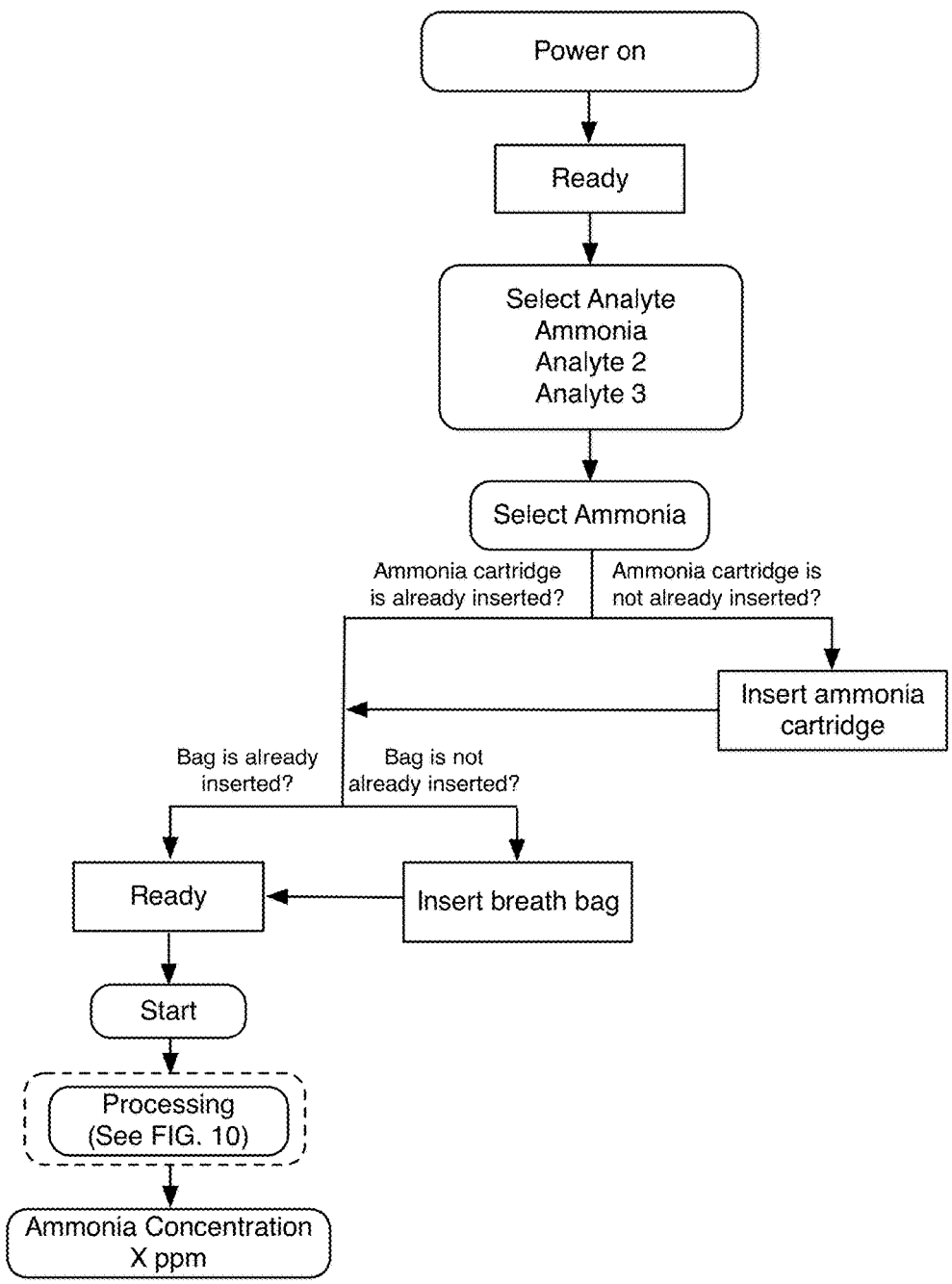
FIG. 9 is an illustrative flow chart for sensing ammonia in a breath sample.
Figure 10:
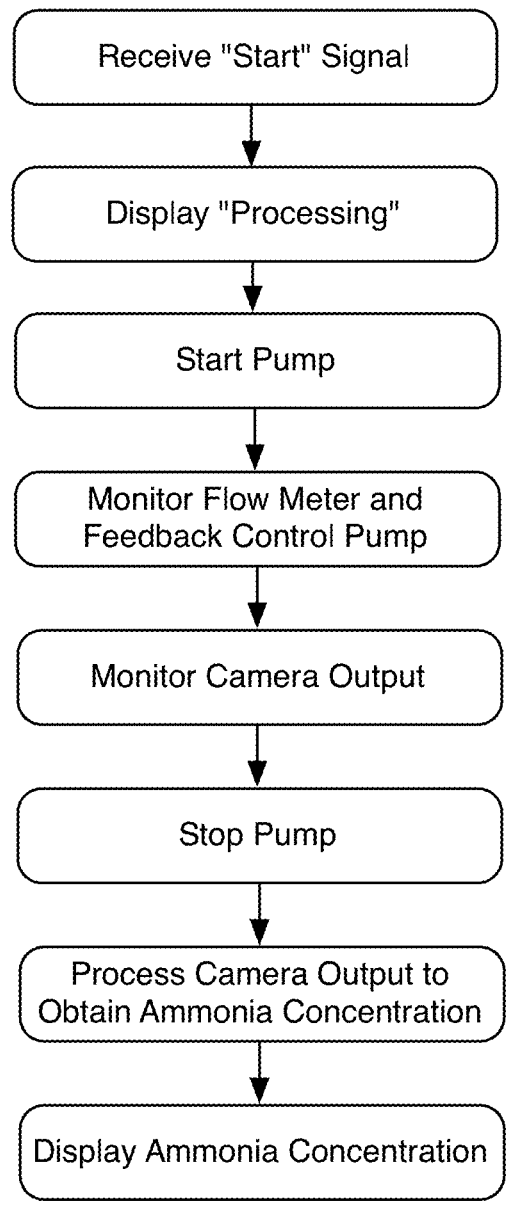
FIG. 10 is another illustrative flow chart for sensing ammonia.

Once the breath sample has been obtained, the preferred method comprises performing the sensing mode, in which base 40 is used to sense the ammonia in the conditioned breath sample. The illustrative method implementation of this sensing mode will now be described with reference to FIG. 9 and FIG. 10. FIG. 9 provides a flow diagram of the user interaction with the base 40 during the sensing mode. FIG. 10 is a flow diagram that shows the principal processing steps performed by processor 194 during the sensing mode. Note that in FIG. 9, blocks with rounded corners indicate actions taken or selections made by the user, whereas blocks with right angled corners represent displays on touch screen 196. The block with hashed line perimeter represents processing by processor 194, which is illustrated in FIG. 10.

With reference to FIG. 9, initially the user or operator of apparatus 10 powers up the base 40 using a standard power switch on base 40 (not shown). Software or firmware within base 40 initializes its electronic components, and displays A "READY" indication on display 196. Processor 194, under the control of software, also presents a query on display 196 asking the user to select which analyte is to be analyzed. In this embodiment and implementation, of course, ammonia is listed as a potential analyte. The user selects "AMMONIA."

Upon this selection, processor 194 checks a sensor input at cartridge receiver 86 to ascertain whether a cartridge is positioned in it. Base 40 also may comprise means to read the cartridge or otherwise ascertain that it is for sensing of ammonia, as opposed to other analytes. If processor 194 detects that an ammonia cartridge is disposed in receiver 86, processing continues. If no ammonia cartridge is detected, however, the software causes display 196 to provide an instruction to the user to insert an ammonia cartridge. At this instruction, the user inserts an ammonia-sensing cartridge 60.

Once an ammonia cartridge is detected as being inserted into receiver 86, processor 194 under the control of the software checks another sensor at input port 42 to ascertain whether a breath bag unit 16b is attached to base 40. If processor 194 detects that a bag unit is coupled to port 42, processing continues. If a bag unit is not detected, however, processor 194 causes display 196 to provide an instruction to the user to attached bag unit 16b. At this instruction, the user bag 16b, which is then detected by processor 194. As bag unit 16b is attached, one-way valve 34 contacts and presses against stanchion or post 42a, whereupon the post lifts the flapper valve and opens the flow path between the interior of bag 18 and flow path 44.

One the processor has confirmed that the bag unit 16b has been properly affixed to port 42, it displays a "READY" indication, and presents a "START" button or option. The user selects this START button, and the processing illustrated in FIG. 10 begins. It should be noted that, in this illustrative but preferred method, all remaining steps and procedures are performed by base 40, without user action or involvement.

Upon selection of "START," processor 194, acting under the control of the software, controls the sensing of the conditioned breath sample as outlined in FIG. 10. In this sensing, the conditioned sample is contacted with the interactant, and any ammonia present in the sample interacts with that interactant to cause a change in the optical characteristic of interest in relation to the amount of ammonia in the sample. As the "START" option is selected and this sensing begins, processor 194 causes "PROCESSING" to be displayed on display 196. It then starts pump 52 at a preset level and monitors flow meter 48. Pump 52 is operated under negative feedback, so that after any initial startup transients, processor causes it to maintain flow at a set level within certain tolerances. The conditioned breath sample flows through column and reaction zone 62 under the influence of pump 52 for a predetermined period of time, e.g., two to three minutes. The duration that pump 52 operates can be determined in a number of ways, for example, until the flow rate across flow meter 48 drops below a predetermined value, until a predetermined level of vacuum arises, etc. In this preferred method implementation, the duration of pump operation is for a predetermined time corresponding to the time required to fully evacuate the bag 18 based on its volume and the flow rate out of the bag. In apparatus 10, for example, bag 18 has a volume of about 450 ml, pump 42 evacuates the bag at a rate of about 150 ml/min. to 200 ml/min. and, for completeness, evacuates the bag as if it had a 500 ml volume. Therefore, pump 42 operates for about two to three minutes.

During the pumping operation, as the conditioned breath sample passes through column 62, and assuming that ammonia indeed is present in the sample, a color change will begin to appear adjacent to the base or upstream end of column 62. This region of the reaction zone 62 where the color change occurs will enlarge and its intensity will increase as additional ammonia reacts with the interactant beads 180.

As the sensing proceeds and these changes occur, camera 190 senses the light from illuminator 192 reflected from this region of the column and stores this information as image data. As the sensing is completed and pump 52 is turned off, and as the process of image data collection is completed, processor 194 processes this image data by obtaining the intensity of the image data that is within a predefined color range. It compares this intensity to a pre-stored base or standard intensity, and thus obtains a change in the measured intensity relative to the base or reference intensity. From this change, the processor uses pre-stored data that correlates the intensity change with a fixed concentration of ammonia. Having obtained the measured or sensed ammonia concentration, processor 194 causes the concentration to be displayed on display 196.

In the ammonia sensing or analysis, the higher the concentration of ammonia in the sample, the greater the extent of the reaction, the higher the concentration of reaction products, and the greater will be the extent of the optical change. In presently preferred embodiments and method implementations, the optical characteristic measured is the intensity of color change. The extent of the change in the optical characteristic as a function of the amount of the ammonia in the breath sample can depend upon a range of factors, including most importantly the specific interactant, the reaction conditions, gas flow rate, etc. These features can be ascertained from the design and calibration of the apparatus.

As was noted herein above, the present inventors have discovered that, although the presence of an excess of water, particularly liquid water is generally undesirable for the aforementioned reasons, the presence of at least some water, particularly water vapor, in some embodiments and applications is not undesirable. Indeed, in some embodiments and applications, including those disclosed herein below, the presence of some level of water in the breath sample is desirable and advantageous, and yields better sensing results. It is even desired in some applications for the sample to include aqueous condensate. Thus, although it is possible for some level of water vapor to be beneficial in such circumstances, preferably the amount of water vapor present during the sensing of the sample is sufficient to cause measurable improvement in the sensing performance of the device or method. Indeed, given that both a complete absence of water vapor in the sample on one hand and an excessive amount of water vapor on the other yield non-optimal results, one may obtain a balanced or optimized amount of water vapor for a particular application that maximizes performance of the measurement.

Although not wishing to be bound by any particular theory or mechanism of operation, the benefits and improvements of providing an appropriate amount or range of water vapor in the prepared breath sample are believed to include the following. In presently preferred embodiments, the ammonia-reactive indicator is deposited onto a dry, hydrophilic support surface. In these embodiments, sufficient residual humidity retained in the breath sample so that, when the breath sample and thus the water vapor in it comes in contact with this surface, some of the water vapor is extracted by or adsorbed onto the surface. This residual humidity, in combination with the hydrophilic surface, has the unexpected benefit of increasing the extraction and adsorption efficiency of the ammonia from breath sample and onto the surface. Once on or generally at the surface, the ammonia reacts with the ammonia-reactive indicator to yield the desired change in the optical characteristic. The increase in extraction and adsorption efficiency is such that, in some cases, the enhancement of the change in the optical characteristic represents a two-fold or more improvement. The higher extraction efficiency leads to less required reagent or interactant and more pronounced optical characteristic change, e.g., darker color changes, with less ammonia. This in turn improves the sensitivity of the reaction.

Figure 11:
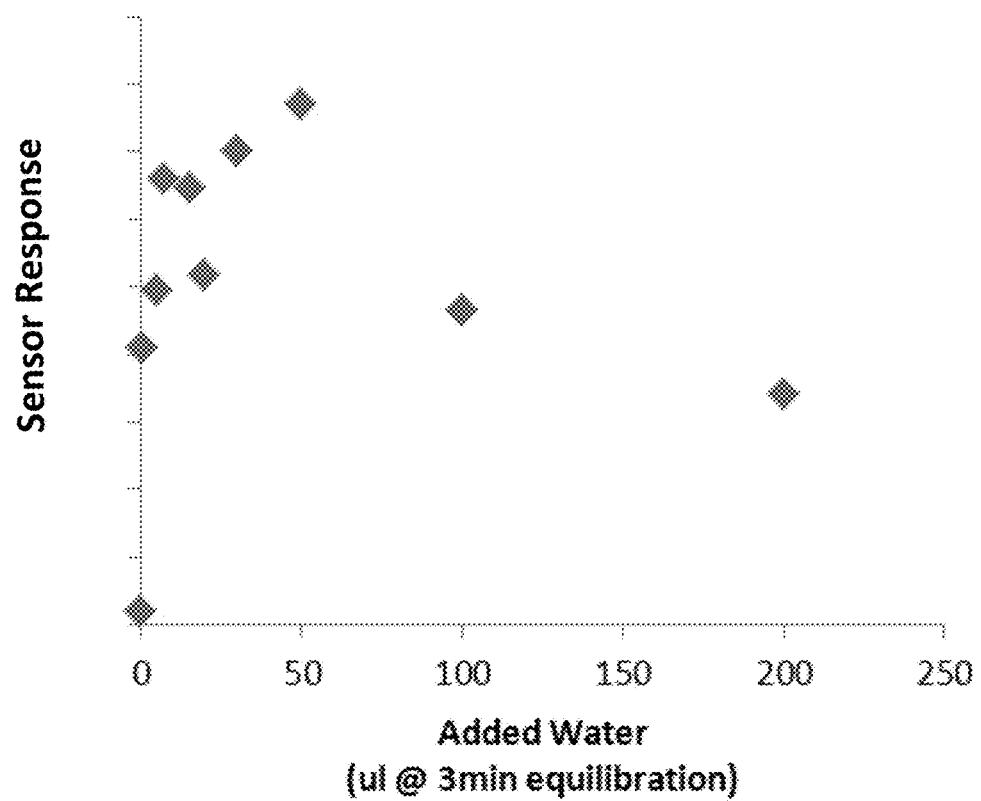
FIG. 11 shows a graph representative of the water content of a population of breath samples.

FIG. 11 is a graph of a curve A representing the output signal, (they axis, corresponding to the measurement of the ammonia concentration generated by a device depicted herein as apparatus 10), obtained by using a gas sample (simulated breath sample) having a composition of 0% $CO_2$, 18% $O_2$, and 2 ppm ammonia, wherein the water content (the x axis) is varied from zero to super-saturation. Given that the curve represents signal variation for a fixed concentration of ammonia, this curve is referred to herein as an "ammonia iso-concentration curve." For each value along the x axis, it is assumed that the water has been in the sample long enough to allow it to reach equilibrium. Accordingly, for water content values at or below saturation, it is assume that the water is present as a vapor, and for water content values above saturation, it is assumed that some amount of condensed, liquid-phase water is present in addition to water vapor. As the curve in FIG. 11 reflects, the signal response is zero or very near to zero when the water content of the sample is at zero. As small amounts of water are increased in small increments from zero, the signal response increases steeply until, at some relatively low level of moisture, the curve flattens and reaches a maximum. Beyond that peak, the curve gradually declines. At different ammonia concentrations, the curve has the same general shape, but is shifted higher or lower depending on the ammonia concentration.

Although not wishing to be held to any particular theory of operation, the shape of the ammonia iso-concentration curves are believed to be the result of at least two competing phenomena underlying the operation of the apparatus and underlying the methods of use according to the invention. One of those phenomena is the ammonia stripping issue described herein above. The other is what is generally referred to herein as a "mobility" issue. These competing phenomena will now be explained, for example, with reference to FIG. 12.

Figure 12:
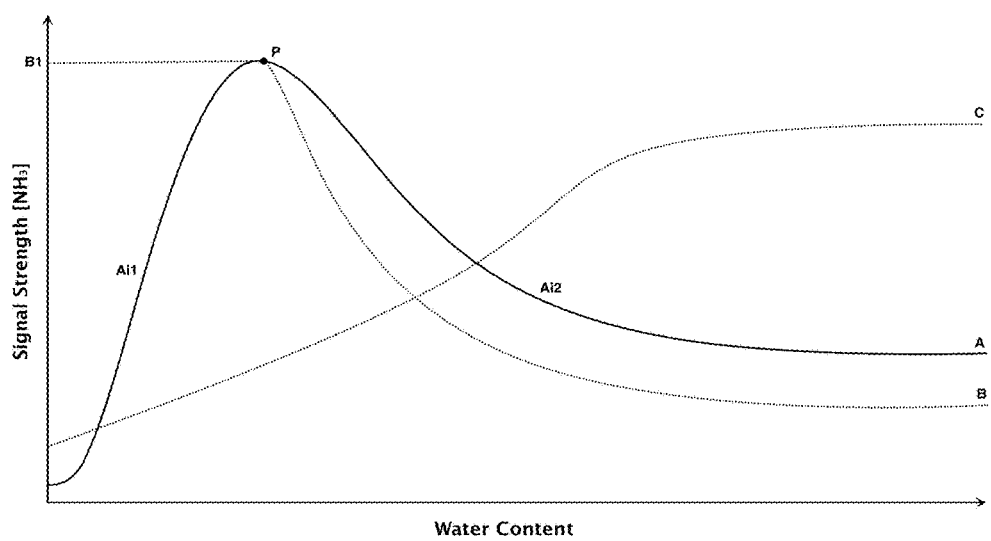
FIG. 12 shows a graph including the ammonia iso-concentration curve with additional curves overlain on it.

In the graph shown in FIG. 12, in which the x axis again represents water content of the breath sample and the y axis again represents the signal strength as measured by the apparatus, and thus representative of the sensed ammonia concentration, the ammonia iso-concentration curve A of FIG. 11 is shown. Overlain on it are curves B and C. Curve B represents the phenomenon of ammonia stripping by water in sample or in the system. As Hamilton and others have recognized, water has the effect of stripping out the ammonia in the gas phase. When there is little or no water in the sample to strip the ammonia (x=0), the signal expected from the system is relatively strong. This strength continues to increase as the water content, in the form of water vapor, increases. At a point B1, the water content reaches saturation, at which point condensation begins to occur and liquid water is present in the sample. Beyond this point B1, increases in water content constitute increases in liquid water, and correspondingly, increases in ammonia stripping.

Curve C represents the competing phenomena of mobility. According to this mobility theory, the presence of some level of water, and particularly water vapor, aids in the sensing of ammonia by enhancing the mobility of the ammonia molecules to the reaction sites and promoting the sensing reaction. Accordingly, this added mobility starts relatively low at or near zero water content (x=0), but increases as water content is increased.

Curve A is in a sense a composite of curves B and C. Although not necessarily strictly additive, the overall system signal (curve A) embodies both of the competing effects of curves B and C.

Several features of curve A are noteworthy. One is its initial value. When no water is present in the system (x=0), the signal normally will not also be zero. Even with no water in the system, some of the ammonia in the gas phase will contact the interactant and give rise to a positive signal value. As curve A increases from its value at x=0, it reaches an ascending or "first" inflection point Ai1. As it proceeds past this first inflection point, it reaches a peak P (corresponding to point B1 on curve B but not necessarily coincident with it). At this point P, the signal has reached its maximum, and under the competing phenomenon theory described herein, the underlying signal strength coupled with the ammonia mobility effect have overcome the ammonia stripping effect. As one proceeds on curve A past peak P, the stripping effect begins to predominate, and the signal falls as water content increases. As one proceeds on curve A beyond peak P, a descending or "second" inflection point Ai2 is encountered.

Figure 13:
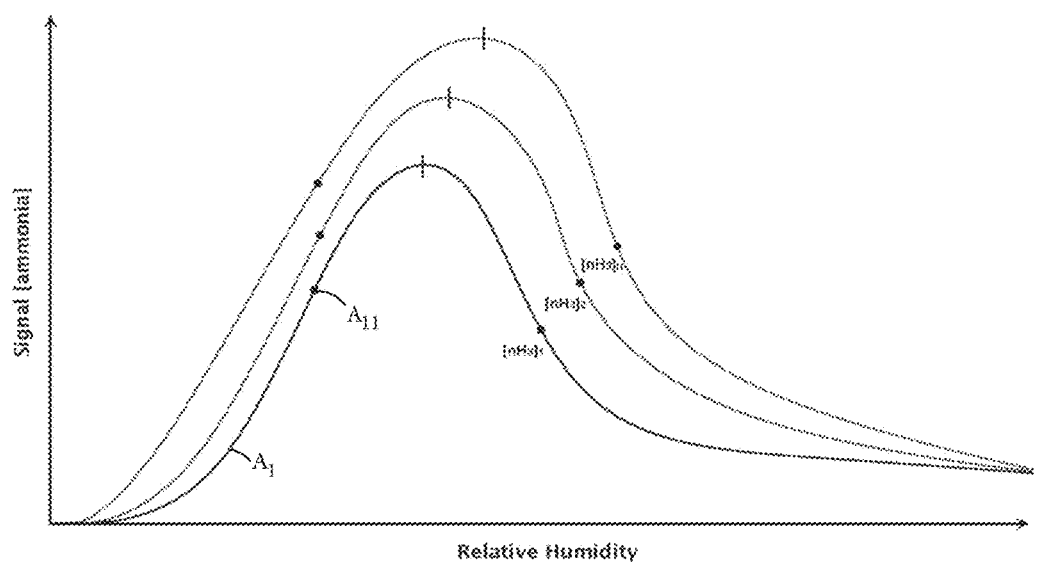
FIG. 13 shows a graph including a plurality of iso-concentration curves.

Although the general shape of the ammonia iso-concentration curves and the underlying phenomenology can be expected to be the same for various concentrations of ammonia over the ranges of interest, the signal strengths at higher ammonia concentrations of course would be expected to be higher than the strengths at lower concentrations. FIG. 13 shows a set of ammonia iso-concentration curves for breath samples with a respective range of ammonia concentrations A1, A2, A3, and A4, each having a successively higher ammonia concentration that its predecessor. In a given device, such as apparatus 10, the device is designed or configured to measure ammonia over a set range of concentrations. Apparatus 10, for example, is designed to measure ammonia in breath samples wherein the ammonia concentration ranges from as low as 0.1 ppm to as high as 20 ppm. Within this range of concentrations, and for a fixed set of concentration levels within the range, a single ammonia iso-concentration curve can be constructed. In apparatus 10, for example, an ammonia iso-construction curve can be constructed for each of the ammonia concentrations [NH3] =10 ppm, as is shown in FIG. 13. Given this range and given the device design, the lowest ammonia iso-concentration curve (at [NH3]=0.1 ppm) can be used to select a lower water content or relative humidity level that is desired or appropriate for the device. Similarly, the highest ammonia iso-concentration curve (at [NH3]=20 ppm) can be used to select an upper water content or relative humidity level that is desired or appropriate for the device.

Using this sensing framework, various ranges of water content or relative humidity and operating regimes can be selected in accordance with the invention to improve or optimize the detection and sensing of ammonia in a breath sample.

In addressing and selecting desired ranges, several factors should be considered. One involves the signal strength or, similarly, signal-to-noise ratio. Ideally, one wishes to operate the device, and use water content levels or relative humidity ranges, that provide a strong, easily discernible signal. Another factor involves the pre-filter. Lower water content levels or ranges generally place greater requires on the pre-filter, e.g., such as requiring more desiccant, more cross sectional area or size, and the like. This can increase the component cost, complexity, and other constraints. More desiccant for a given size also can increase the flow resistance of the pre-filter, thus making use of the device more difficult and potentially unpleasant for the patient. Conversely, operating at higher water content ranges generally implicates fewer, less onerous and less costly pre-filter designs.

When considering the water content or relative humidity range for the device overall, one normally focuses on the two extremes: (1) the lower extreme or limit of the range for the device, which normally will involve selection of an appropriate minimum water content or relative humidity for the lowest concentration of ammonia that the device is designed to detect or measure, and (2) the upper extreme or limit of the range for the device, which normally will involve selection of an appropriate maximum water content or relatively humidity for the highest concentration of ammonia that the device is designed to detect. In the first instance, i.e., the lower limit, one normally would use the ammonia iso-concentration curve for the lowest ammonia concentration that one expects to detect or measure with the device. With reference to FIG. 13, this is curve A1. One normally would select a point on curve A1 that corresponds to the signal strength (y value) and associated water content or relative humidity value (x value) that will be recognized as being a clear and correct positive detection of that concentration of ammonia.

This selection preferably is made by considering and balancing the desire or need for sufficient signal strength and confidence, e.g., considering such factors as those below, against a need or desire to keep the size, flow resistance, cost, etc. of the pre-filter at or below certain threshold values. Examples of criteria for obtaining sufficient signal strength would include the following: (a) a signal above a minimum threshold signal level, (b) a signal above a minimum threshold signal-to-noise ratio, (c) a signal that is some predetermined percentage of the peak value for that iso-concentration curve, and (d)

In considering this method and its underlying considerations, it will be clear that various water content or humidity ranges could be selected, depending upon such factors as the desired ammonia concentrations sought to be sensed (or for which the device is capable of sensing), the sizes of the relative components, and the detection sensitivity or resolution for detection of various concentrations.

Preferably, the breath sample is conditioned so that it has a water content or relative humidity corresponding to a maximum change in the optical characteristic. Because it may be difficult to specifically set for the maximum itself, one may set the level at a fixed range or tolerance around the maximum.

In one preferred implementation, for example, and with reference to FIG. 13, the lower limit of the range for the water content or relative humidity of the conditioned breath sample is the water content or relative humidity corresponding to the first inflection point $A_{11}$ of the lowest ammonia iso-concentration curve $A_1$. This first inflection point on the lowest iso-concentration curve corresponds to a region in which the beneficial effects of mobility are strong, but at which the deleterious effects of ammonia stripping have not yet made a significant adverse impact. It should be noted that, at points on curve A1 further to left of the first inflection point A11, the curve is very steep and its angle is increasing with x. Thus, small increases in water content give rise to relatively large increases in signal strength.

In another preferred implementation, the lower limit for the water content or relative humidity of the conditioned breath sample is that corresponding to the peak A1P of the first iso-concentration curve. At this peak, much of the beneficial effects of mobility have been obtained, and any further water content will bring pronounced negative effects from ammonia stripping. Any further water content beyond this peak point of curve A1 would be expected to produce condensation that would rapidly strip ammonia from the gas phase and decay the detection quality of the device.

In yet another preferred implementation, the lower limit of the range for the water content or relative humidity of the conditioned breath sample is that corresponding to the second inflection point $A_{12}$ of the lowest ammonia iso-concentration curve $A_1$. This second inflection point on the lowest iso-concentration curve corresponds to a region in which the beneficial effects of mobility have been fully utilized, and in which some condensation and correspondingly deleterious effects of ammonia stripping have occurred, but in which the requirements for desiccation by the pre-filter have been sufficiently relaxed to offset the disadvantages of the stripping, and wherein the water content level is not so high that the signal strength has been unacceptably degraded. Using this same logic, one could select any of the various points along curve A1 between peak A1P and second inflection point A12 to obtain similar balance between these advantages and disadvantages.

Another suitable and sometimes desirable lower limit for water content or relative humidity is the first midpoint Ala that is half of the distance along the lowest ammonia iso-concentration curve A1 between the first inflection point A11 and peak A1P of curve A1. This point lies sufficiently above the first inflection point, which is less desirable in some cases based on the steepness of the curve A1 at that point and the corresponding sensitivity of signal strength to relatively small variations in water content. It is sufficiently below the peak A1P so that it provides a margin of safety before condensation is expected to occur.

The upper limit for water content or relative humidity in the conditioned breath sample for a given device also preferably is based on the lowest ammonia iso-concentration curve A1. This is because, even though the ammonia iso-concentration curves for the higher ammonia concentrations can tolerate greater amounts of water, permitting the device overall to accept these higher water content levels will interfere with the most sensitive, low level concentrations of ammonia, corresponding to the lowest iso-concentration curve. Therefore, one preferably selects a suitable upper limit for the water content or humidity based on the lowest curve A1, and if higher ammonia concentrations are found, one merely obtains the signal strengths of the higher iso-concentration curves corresponding to that water content.

The peak A1P of the lowest ammonia iso-concentration curve A1 provides a useful and in many cases preferred upper limit for the water content or relative humidity. As explained herein above, it represents a point at which advantage has been taken of the beneficial effects of mobility, but before pronounced negative effects from ammonia stripping have occurred.

The second inflection point A12 on the lowest iso-concentration curve A1 also presents a suitable in sometimes preferred upper limit for the water content or relative humidity. As noted above, it corresponds to a region in which the beneficial effects of mobility have been fully utilized, and in which some condensation and correspondingly deleterious effects of ammonia stripping have occurred, but in which the requirements for desiccation by the pre-filter have been sufficiently relaxed to offset the disadvantages of the stripping, and wherein the water content level is not so high that the signal strength has been unacceptably degraded.

The midpoint A1*b* of the lowest ammonia iso-concentration curve A1 also provides a suitable and sometimes desirable upper limit for water content. It has the advantages noted above regarding the peak value, and gains further advantage regarding the relative simplicity and lower cost of the pre-filter, but does not extend into the region to the right at which ammonia stripping is predominant and signal strength is substantially degraded.

In some instances, it is preferably to have a water content or relative humidity that is bounded on both ends, i.e., a lower bound and an upper bound. In such instances, various combinations of the lower and upper bounds provided herein above would be useful, for reasons including those set forth above.

These ranges can be implemented through the design and construction of the pre-filter, the use of a secondary conditioner, by inclusion of water in the reaction vessel, or some combination of these.

A variety of methods and techniques can be employed to reduce the humidity within the breath sample to a level where condensation (liquid water) is minimized or brought to a desired level or range, and water vapor concentration is optimized. One such method involves passing the breath sample through a hygroscopic substance or desiccant, e.g., such as anhydrous $CaCl_2$, NaOH and Ascarite, such as are commonly available from chemical suppliers such as Sigma Aldrich. Anhydrous $CaCl_2$ readily removes water from the breath sample, but also may remove some of the ammonia. NaOH is effective for removing both water and $CO_2$, but it is deliquescent. Ascarite II also is effective at removing water and $CO_2$, and, because of its vermiculite core, is not prone to complete dissolution. Further, a dye in Ascarite II provides visualization for the removal of water/$CO_2$ from the breath sample, making it easier to determine how much should be used.

Preferably but optionally, the humidity is removed from the breath sample before or immediately upon leaving the mouth. The flow path to the desiccant and the surface area of any filters holding the desiccant preferably are minimized to limit or reduce condensation and extraction of ammonia prior to contact with the desiccant.

Some desiccant materials, e.g., Ascarite®, comprise or form a fine powder that can pose a risk of injury to patients if inhaled, ingested, or the like. Attempts to address this risk by using particulate filters often are unsatisfactory because they promote condensation and strip out ammonia. Accordingly, in the presently preferred embodiments and method implementations, preferably use is made of a non-powder forming alkaline desiccant with a relatively large mesh size, as described herein above, enabling the use of small surface area filters with minimum hazard of condensate formation. In presently preferred embodiments, the non-powder forming alkaline desiccant is anhydrous sodium hydroxide crystals with a mesh size of between about 4 and 30, and more preferably between about 20 and 30. Sodium hydroxide and related salts do not form the dangerous powder present in Ascarite and do not require a thick, high surface area filter. Rather, they can be used with a thin filter, between about 0.0001" and about 0.01", and more preferably between about 0.0005" and about 0.003", with large pore sizes, between about 30×30 mesh and about 300×300 mesh, between about 60×60 and about 230×230 mesh.

In designing and operating devices according to the present invention, it is desirable and in some cases necessary to limit or eliminate any liquid-phase water in the conditioned sample that enters the interactant column. There are a number of methods and approaches to achieving this goal.

To the extent there is any water vapor in the breath sample, any decreases in the temperature of the sample brings the risk that some portion of that vapor will condense. Relative humidity, of course, is a function of temperature, and for a given volume and pressure of gas at equilibrium, warmer gas has a greater capacity for vapor than does a cooler gas. Under normal circumstances of operation, i.e., wherein the original breath sample is at human body temperature of about 37° C., and wherein the breath bag or container is at or about ambient or room temperature, e.g., 25° C., there is an inherent risk of condensation.

To limit condensation of the water vapor and possibly to reduce the amount of condensed water, one may heat the breath sample. This may be done, for example, by heating bag unit 16b, by heating base 40, or preferably, both. The heating of the sample in the base before it enters the column 62 is particularly important because, even if heating occurs at the bag unit 16b, there still will be opportunities in the base and elsewhere for the sample to be subsequently cooled and thus condense. Preferably this heating will cause the breath sample to have an average or mixing cup temperature of at least 37° C. When this heating approach is used, the temperature must be maintained to avoid re-condensation.

In an illustrative embodiment for achieving this feature, the bag would be stored prior to use in a heated container, such as an autoclave-type device maintained at a temperature of at least several degrees above ambient temperature, and preferably at or near 37° C.

It would also be desirable if not necessary to maintain an elevated temperature in the base 40 and cartridge 60 to obtain optimum results. This could be achieved in a modification of apparatus 10, for example, that comprises two 5-watt silicone pressure sensitive adhesive ("PSA") heaters 54a and 54b placed in the base 40 and configured to heat breath the conditioned breath sample, for example, at or near input port 42 and in flow path 44 at or adjacent to cartridge 60 and specifically column 62. The heaters then are set so that they generate an appropriate amount of heat to maintain these components at a temperature of at least a few degrees over ambient temperature, e.g., using a commercial temperature controller, an analog setpoint circuit, or the like.

Changes in the pressure of the breath sample also can force water vapor in the sample to condense. Accordingly, effort should be made to avoid any pressure increases in the sample as it travels through base 40 that would induce such condensation.

Risks of unwanted condensation are particularly great where the flow characteristics of the breath sample change. With reference to apparatus 10, for example, such regions occur at flow modifier 50, pump 52, and in column 60 itself. This is why pump 52 in this embodiment is positioned downstream from flow modifier 50 rather than upstream. As the pump pulses and corresponding pressure increases are encountered during its normal cycling, flow modifier 50 absorbs this overpressure, functioning in a sense as a condenser or pressure damper. Flow modifier can perform this function as long as it is in the flow path 44, whether upstream or downstream of pump 52. If flow modifier 50 were downstream of pump 52, however, the overpressure transients from pump 52 in combination with the flow resistance associated with flow modifier 50 would tend to create enhanced pressure, and thus increase the risk of unwanted condensation.

EXAMPLES

The following examples provide informative but merely illustrative embodiments and method implementations to further describe and explain various aspects of the invention.

Example 1: Bead Synthesis

In a 50 ml conical vessel, 200 uL of 0.1 N HCl was added to 4 mL of 1:10 dilution of saturated bromophenol blue in 2-propanol. 1.80 g of 35 to 60 mesh Davisil silica beads, pore size 60 angstroms, was added to the mix and mixed thoroughly. After 10 minutes incubation at room temperature, the beads were mixed again and placed on a hotblock with an actual temperature of 80° C. for 25 minutes. The beads were still sticky when removed. They were vortexed for a few seconds to mix them, and then placed under vacuum for 1 hour to finish drying. The beads this process yielded were homogenous in appearance. The beads were immediately aliquoted into 60 individual 1.5 ml Eppendorf tubes and stored at −20° C.

The following observations were made regarding the reactivity and selectivity of the substrate beads of Example 1. When pure acetone was added to the beads, no color change was observable. No color change was caused by 100% relative humidity at 37° C., or by 5% $CO_2$ or by 18% $O_2$, or by any combination of these. Unless the humidity is extracted, 100% relative humidity at 37° C. will result in condensation at lower temperatures.

Ammonia was extracted by condensation to form ammonium hydroxide. The condensation was slightly acidic in the presence of carbon dioxide, increasing the extraction of ammonia, and potentially forming ammonium carbonate and related salts. The problem is compounded when the sample is passed across high surface area materials like filters, beads or porous material. Ammonia, however, is not significantly extracted by condensation under alkaline conditions.

Example 2: Ammonia Detection

Beads from Example 1 were placed in a 1.2 mm inside diameter glass tube about 0.75" inches length. An Ascarite II column (0.25" id, 0.7" long) was attached to the front of the glass tube. A flow rate of 225 ml/min. was used with a total volume of 900 mL. Ammonia in simulated breath (100% relative humidity, 18% $O_2$, 5% $CO_2$ in $N_2$) collected in a Tedlar® bag was consistently detectable at levels below 50 ppb. The color change at 50 ppb was dark.

Example 3: Bead Synthesis Using $H_2SO_4$

In a 50 ml conical vessel, 7 uL of 1 N $H_2SO_4$ were added to 2 mL of 1 mg/ml solution of bromophenol blue in 2-propanol. 1.0 g of 35 to 60 mesh Davisil silica beads, pore size 60 angstroms, were added to the mix and vortexed thoroughly. Beads were incubated at 80° C. for 10 minutes with the lid on. The lid was then removed and the beads were incubated at 80° C. for another 45 minutes. The beads were vortexed once every 10 to 20 minutes during this incubation period. The beads were then incubated at 110° C. for about 45 minutes, vortexing every 10 to 20 min, until no more condensation appeared on a lid at room temperature. The beads thus produced were homogenous in appearance. They were immediately aliquoted into 80 individual 1.5 ml Eppendorf tubes and stored at −20° C.

Example 4: Desiccant

Beads made as described in Example 1 were loaded into a 1.2 mm inside diameter column. 900 ml of 0.2 ppm ammonia in 5% $CO_2$, 18% $O_2$, and varying humidity was passed across the beads at 225 ml/min. with and without a 0.25" inside diameter column having 0.7" length filled with Ascarite II®. When 50% relative humidity at 37° C. was used with no Ascarite II®, a concentrated, short segment was visible in the reaction vessel. When the relative humidity was increased to 100% at 37° C., however, no color change was observed. When the 100% relative humidity sample was passed across the Ascarite II column, the signal was restored.

Example 5: Stability

Beads made in Examples 1 and 3 were compared for stability in an accelerated aging study using an oven at 102° C. Approximately 50 mg of each type of beads were placed in 1.5 ml tubes in triplicate. A porous membrane was placed over the beads and Ascarite II was added. The tubes were sealed and placed in the oven. The beads made with HCl (Example 1) had a visible color change after several hours. The beads made with $H_2SO_4$ (Example 3) lasted 48 hours, implying up to a 10 fold increase in stability over those of Example 1.

Example 6: Bead Sensitivity Using $H_2SO_4$

In three 50 ml conical vessels, 6, 7 and 8 uL of 1 N $H_2SO_4$, respectively, was added to 2 mL of 1 mg/mL solution of bromophenol blue in 2-propanol. 1.0 g of 35 to 60 mesh Davisil silica beads, pore size 60 angstroms, were added to each mix and vortexed thoroughly. The beads were incubated at 80° C. for 10 minutes with the lid on. The lid was then removed and the beads were incubated at 80° C. for another 45 minutes. The beads were vortexed once every 10 to 20 minutes during this incubation period. The beads were then incubated at 110° C. for about 45 minutes, vortexing every 10 to 20 minutes, until no more condensation appeared on a lid at room temperature. The beads thus produced were homogenous in appearance. They were immediately aliquoted into 80 individual 1.5 ml Eppendorf tubes and stored at −20° C.

The beads with 6 microliter ("ul") 1 N $H_2SO_4$ were slightly darker in appearance. However, they still maintained their characteristic yellow color. The signals generated by 0.25 ppm ammonia on beads made with 6, 7 and 8 ul $H_2SO_4$, respectively, were compared. The signal increased substantially when less acid was used.

Example 7

Figure 14:
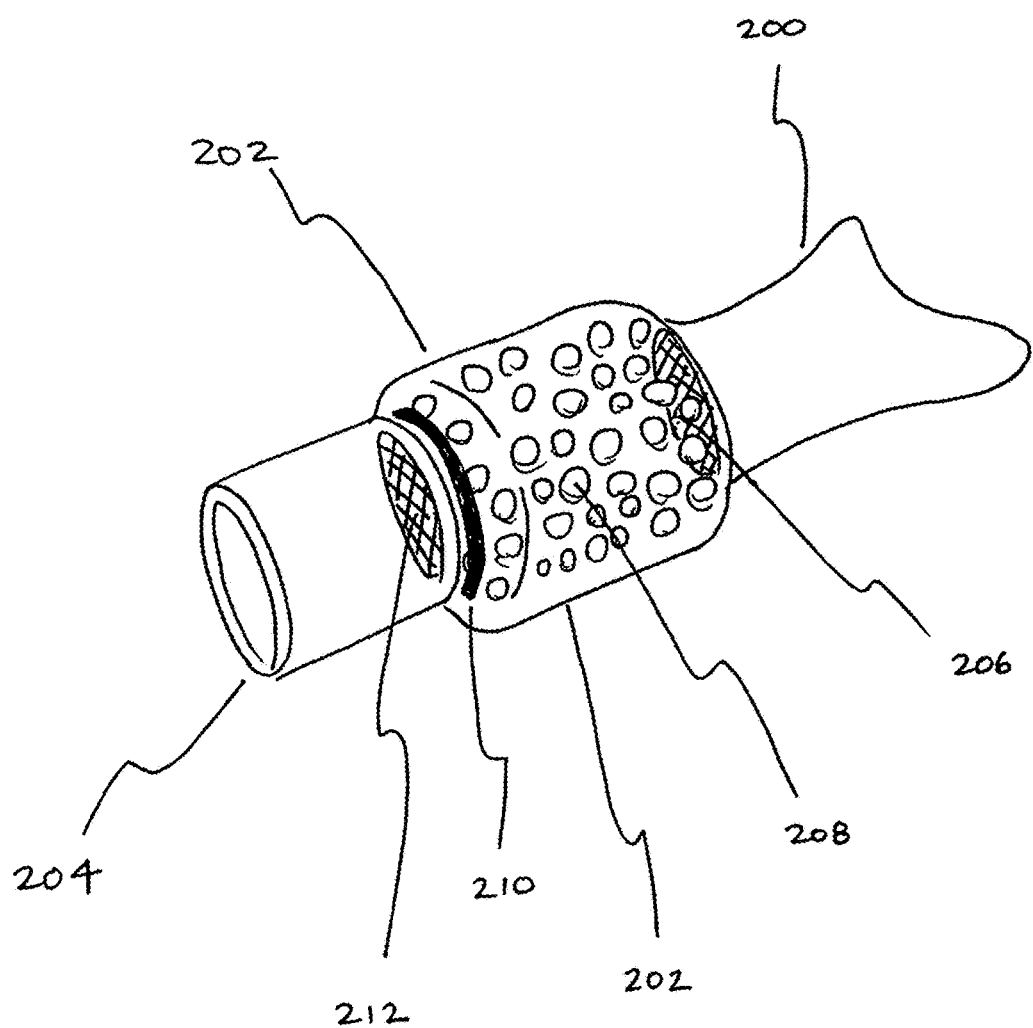
FIG. 14 shows an embodiment of a pre-filter.

FIG. 14 shows an apparatus for removing humidity from breath. A plastic housing (202) is formed with an integral mouthpiece (200). A stainless steel mesh disk (200×200 mesh, 1" diameter) is attached onto an aperture array surface (214) within the plastic housing (202). Attachment is made by heat-pressing the mesh into the plastic surface or by using other means such as accessory compression fit devices such as an o-ring (see FIG. 15). Next, the plastic housing (202) is filled with a desiccant medium, for example sodium hydroxide pellets (208). Next, a compressible porous medium (210) such as fibrous polyethylene (⅛" thick, 1" diameter) is placed over the packed desiccant medium (208) and the bag adapter piece (204) is welded or otherwise attached to the housing (202), causing the desiccant medium (208) to be tightly and immovably packed into the housing (202). The compressible porous medium (210) is kept in position by a second aperture array surface (212).

Example 8

Figure 15:
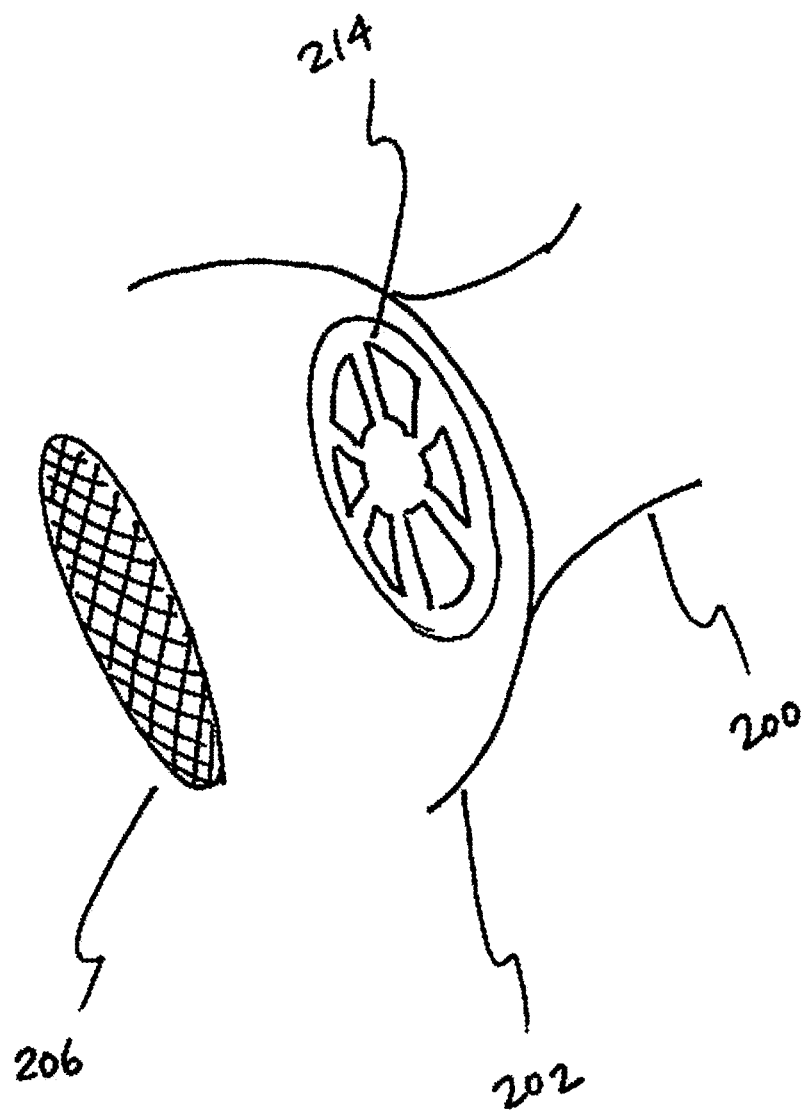
FIG. 15 shows an enlarged portion of the embodiment of the pre-filter shown in FIG. 14; and, FIG. 16 shows a breath bag that can be used for sensing ammonia.
Figure 16:
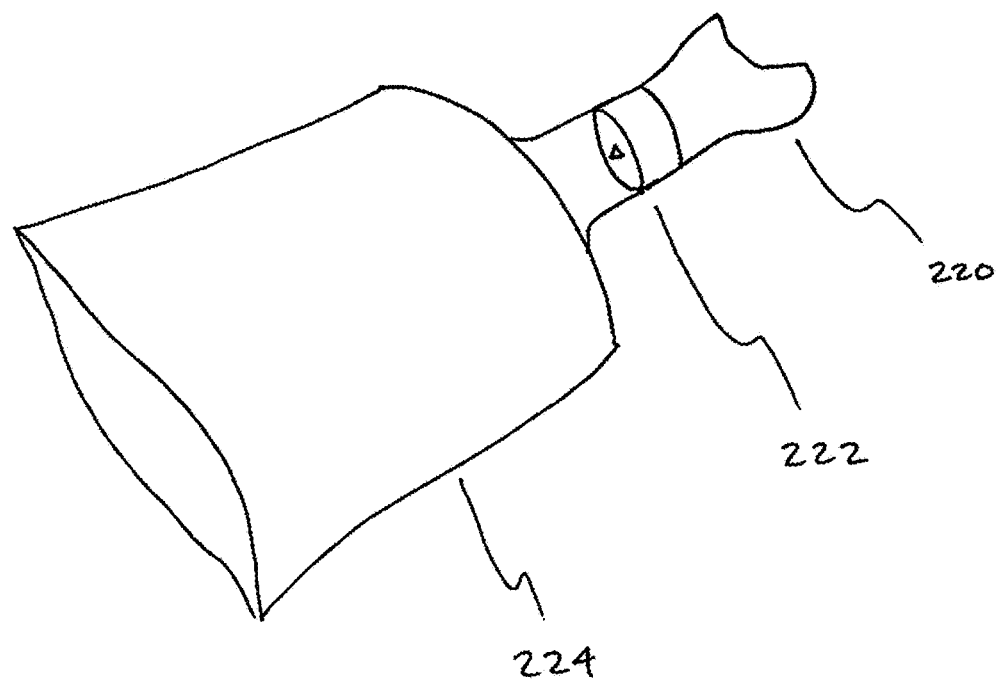

FIG. 15 shows an apparatus for removing humidity from breath. A bag (224) is fitted with a one-way valve (222), such as a flapper valve, and a detachable mouthpiece (220). The inside surfaces of the bag walls have been treated with moisture adsorbents, for example sodium hydroxide impregnated cellulose paper. This embodiment offers the advantage of low breathing resistance through the pre-filter element and a longer contact time between the desiccant and breath sample.

Example 9

An apparatus for removing humidity from breath was prepared as illustrated in FIG. 14. A stainless steel mesh (300×300 mesh) was used to retain 20-30 mesh Ascarite II particles on the breath inlet side. The stainless steel mesh disk was held in place using a 1" o-ring which pressed against the side walls and the mesh disk. A porous polyethylene disk (1" diameter, ⅛" thick) was used to tightly press the Ascarite II particles into the housing. The housing comprised a cavity 1" deep by 1" diameter which attached to the bag adapter using threads. Three such devices were assembled and the water content and carbon dioxide content extant in attached breath bags after users blew into the bag was assessed with a gas chromatograph.

It will be appreciated that the invention is not limited to the specific embodiments and method implementations described herein. The description herein has largely been explained with respect to human patients or subjects, but this is not necessarily limiting. The principles of the invention also may be applied in veterinary applications.

We claim:

1. A method for sensing ammonia in a breath sample, the method comprising:
    conditioning the breath sample so that the conditioned breath sample has a relative humidity greater than a relative humidity corresponding to a first inflection point of a downwardly concave portion of an ammonia iso-concentration curve, wherein conditioning the breath sample comprises passing the breath sample through a granular desiccant to reduce the relative humidity;
    contacting the conditioned breath sample with an interactant that interacts with the ammonia in the conditioned breath sample, wherein the interaction causes a change in an optical characteristic in relation to the amount of the ammonia in the breath sample;
    sensing the change in the optical characteristic with a sensor, wherein the sensor generates an output signal representing the change in the optical characteristic; and
    by a processor, using the output signal representing the change in the optical characteristic to determine a concentration of the ammonia in the breath sample.

2. A method as recited in claim 1, wherein the conditioning of the breath sample comprises conditioning the breath sample so that the conditioned breath sample has a relative humidity corresponding to a maximum change in the optical characteristic.

3. A method as recited in claim 1, wherein the interactant comprises an ammonia-reactive indicator that changes color as ammonia interacts with the ammonia-responsive indicator.

4. A method as recited in claim 3, wherein the ammonia-reactive indicator comprises a pH indicator.

5. A method as recited in claim 3, wherein the silica gel substrate has a mesh size of between 20 and 200.

6. A method as recited in claim 1, wherein the interactant comprises a pH indicator coupled to a silica gel substrate.

7. A method as recited in claim 1, wherein the optical characteristic comprises an intensity at a predetermined optical frequency.

8. A method as recited in claim 1, wherein the optical characteristic comprises an intensity at a predetermined range of optical frequencies.

9. The method of claim 1, wherein the granular desiccant is an alkaline desiccant.

10. The method of claim 1, wherein the granular desiccant has an alkalinity greater than an alkalinity of ammonia.

11. The method of claim 1, wherein conditioning the breath sample further comprises heating the breath sample.

12. An apparatus for sensing ammonia in a breath sample, the apparatus comprising:
    a breath conditioning device configured to receive the breath sample and condition the breath sample so that the conditioned breath sample has a relative humidity greater than a relative humidity corresponding to a first inflection point of a downwardly concave portion of an ammonia iso-concentration curve, wherein the breath conditioning device comprises at least one of (1) a granular desiccant through which the breath sample is passed to reduce moisture in the breath sample, or (2) a heater that heats the breath sample;
    an interactant region configured to receive the conditioned breath sample and to cause the conditioned breath sample to interact with an interactant that interacts with the ammonia in the conditioned sample wherein the interaction causes a change in an optical characteristic of the interactant region in relation to the amount of the ammonia in the breath sample;
    a sensor that senses the change in the optical characteristic and generates an output representative of the change in the optical characteristic; and
    a processor operatively coupled to the sensor, the processor configured to use the output to assess at least one of the presence and the amount of the ammonia in the breath sample.

13. An apparatus as recited in claim 12, wherein the processor is configured to use the output of the sensor to determine a concentration of the ammonia in the breath sample.

14. An apparatus as in claim 12, wherein the breath conditioning device comprises the granular desiccant through which the breath sample is passed to reduce moisture in the breath sample.

15. An apparatus as in claim 12, wherein the breath conditioning device comprises the heater that heats the breath sample.

16. A method for making a breath sensing device for sensing ammonia in a breath sample, the method comprising:
    coupling an ammonia-reactive indicator to a substrate, wherein the ammonia-reactive indicator has a pKa of less than 8;
    contacting the ammonia-reactive indicator and the substrate with an acid having at least two available protons to form an interactant, wherein the pKa for the dissociation of a first one of the protons is less than the pKa of the ammonia-reactive indicator, wherein the boiling point of the acid in a 99% pure form is greater than 37° C. at standard atmospheric pressure, and wherein the interactant is configured to interact with the ammonia in the breath sample to yield a product, and to cause a change in an optical characteristic between the interactant and the product in relation to the amount of the ammonia that interacts with the interactant; and
    disposing the ammonia-reactive indicator and the substrate in an interactant region of a sensor that is configured to receive the breath sample
    providing a breath conditioning device configured to prepare the breath sample so that the breath sample has a relative humidity greater than a relative humidity corresponding to a first inflection point of a downwardly concave portion of an ammonia iso-concentration curve.

17. A method as recited in claim 16, wherein the ammonia-reactive indicator comprises a pH indicator.

18. A breath sample containing device for use in sensing ammonia in a breath sample using a breath analysis device, wherein the breath analysis device comprises a base with a detachable cartridge comprising an interactant region configured to receive a conditioned breath sample and to cause the conditioned breath sample to interact with an interactant that interacts with the ammonia in the conditioned sample wherein the interaction causes a change in an optical characteristic of the interactant region in relation to the amount of the ammonia in the breath sample, and wherein the base comprises a sensor that senses the change in the optical characteristic and generates an output representative of the change in the optical characteristic, the breath sample containing device comprising:
- a breath sample container comprising a coupler for detachably coupling the breath sample container to the breath analysis device;
- a breath sample input coupled to and in fluid communication with the breath sample container;
- a breath conditioning device configured to receive the breath sample from the input and condition the breath sample so that the conditioned breath sample has a relative humidity greater than a relative humidity corresponding to a first inflection point of a downwardly concave portion of an ammonia iso-concentration curve, the breath conditioning device comprising at least one of (1) a granular desiccant through which the breath sample is passed to reduce moisture in the breath sample, or (2) a heater that heats the breath sample.

19. The breath sample containing device of claim 18, wherein the breath conditioning device comprises the granular desiccant through which the breath sample is passed to reduce moisture in the breath sample.

20. The breath sample containing device of claim 19, wherein the breath conditioning device additionally comprises the heater that heats the breath sample.

21. The breath sample containing device of claim 18, wherein the breath conditioning device comprises the heater that heats the breath sample.

* * * * *